(12) United States Patent  
Gleckler

(10) Patent No.: US 7,534,984 B2
(45) Date of Patent: May 19, 2009

(54) VERY FAST TIME RESOLVED IMAGING IN MULTIPARAMETER MEASUREMENT SPACE HAVING MEANS FOR SEPARATING REFLECTED LIGHT TO FORM PLURAL BEAM IMAGES

(75) Inventor: Anthony D. Gleckler, Oro Valley, AZ (US)

(73) Assignee: Arete' Associates, Northridge, CA (US)

( * ) Notice: Subject to any disclaimer, the term of this patent is extended or adjusted under 35 U.S.C. 154(b) by 0 days.

(21) Appl. No.: 11/809,778

(22) Filed: Jun. 1, 2007

(65) Prior Publication Data

US 2008/0035834 A1      Feb. 14, 2008

Related U.S. Application Data

(62) Division of application No. 10/258,917, filed on Jun. 10, 2003, now Pat. No. 7,227,116.

(51) Int. Cl.
*H01L 27/00* (2006.01)

(52) U.S. Cl. ................... 250/208.1; 250/559.4

(58) Field of Classification Search ............. 250/208.1, 250/559.4, 216, 214 R, 214 VT, 207, 458.1, 250/459.1, 461.1; 382/128–134, 154, 173–175; 356/326, 419, 417, 318
See application file for complete search history.

(56) References Cited

U.S. PATENT DOCUMENTS 3,719,775 A * 3/1973 Takaoka et al. ............. 348/145

* cited by examiner

*Primary Examiner*—Que T Le
(74) *Attorney, Agent, or Firm*—Peter I. Lippman

(57) ABSTRACT

Plural electronic or optical images are provided in a streak optical system, as for instance by use of plural slits instead of the conventional single slit, to obtain a third, fourth etc. dimension—rather than only the conventional two, namely range or time and azimuth. Such additional dimension or dimensions are thereby incorporated into the optical information that is to be streaked and thereby time resolved. The added dimensions may take any of an extremely broad range of forms, including wavelength, polarization state, or one or more spatial dimensions—or indeed virtually any optical parameter that can be impressed upon a probe beam. Resulting capabilities remarkably include several new forms of lidar spectroscopy, fluorescence analysis, polarimetry, spectropolarimetry, and combinations of these.

21 Claims, 23 Drawing Sheets

FIG. 1
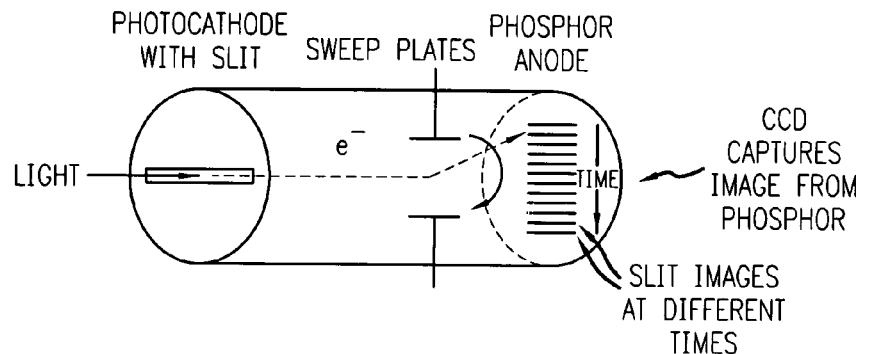
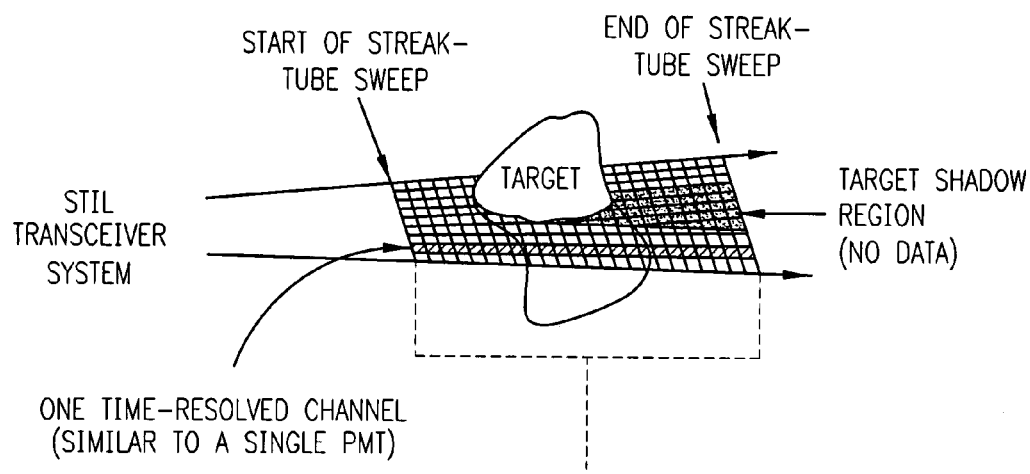
FIG. 2a
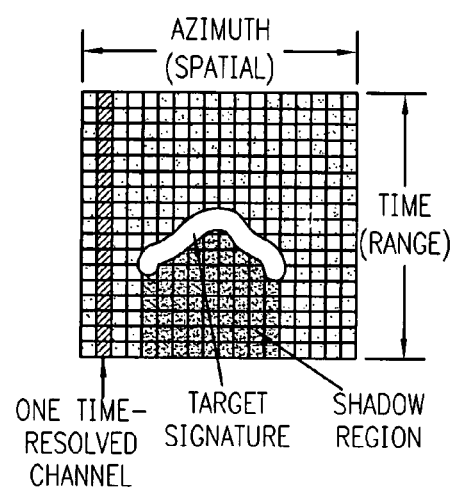
FIG. 2b

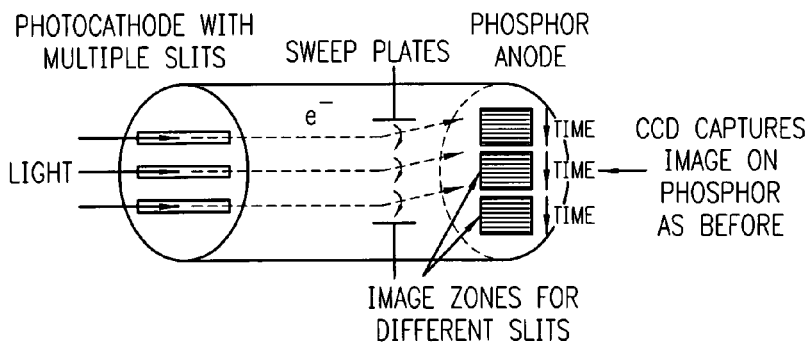
FIG. 7
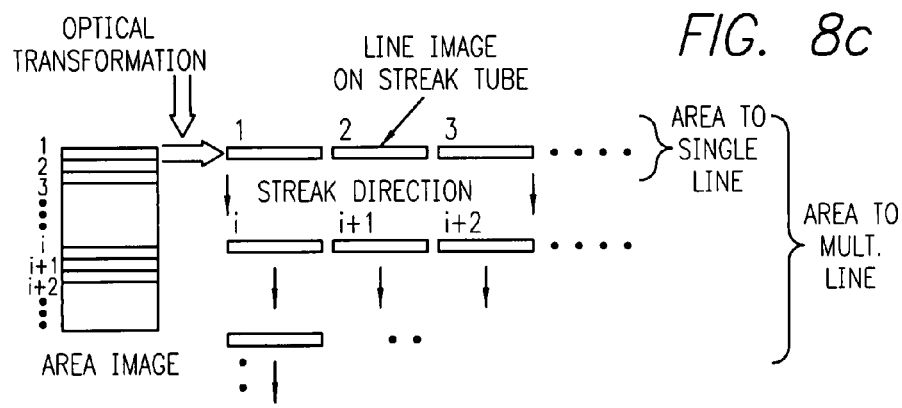
FIG. 8a
FIG. 8b
FIG. 8c
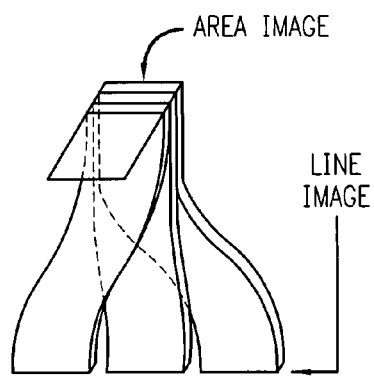
FIG. 8d

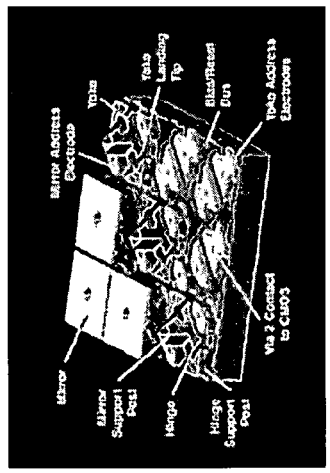
FIG. 11c
FIG. 11b
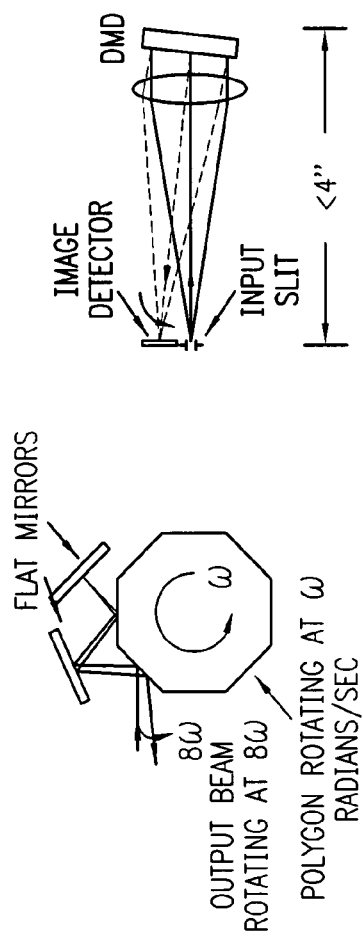
FIG. 11a
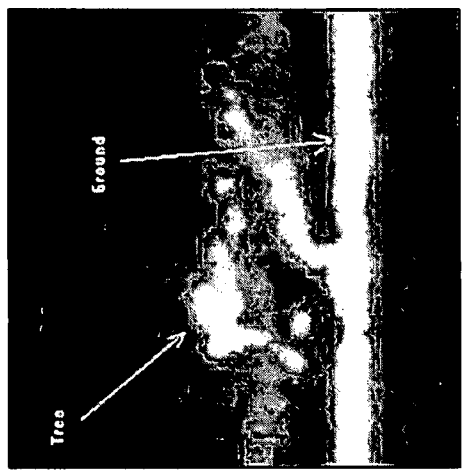
FIG. 20b
FIG. 20a

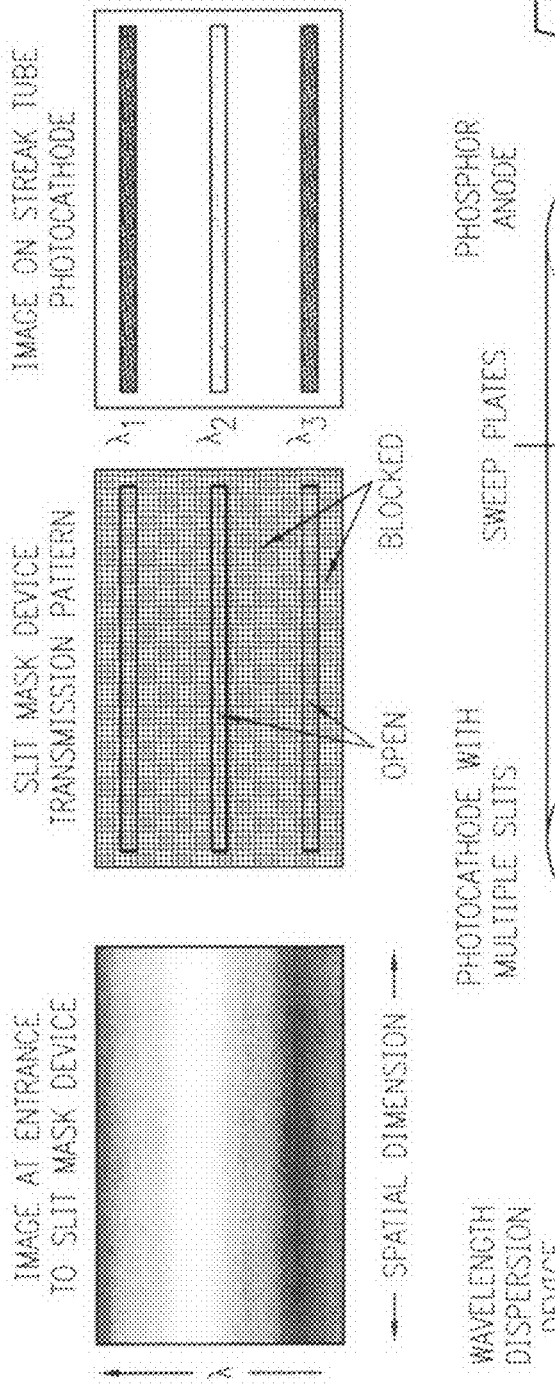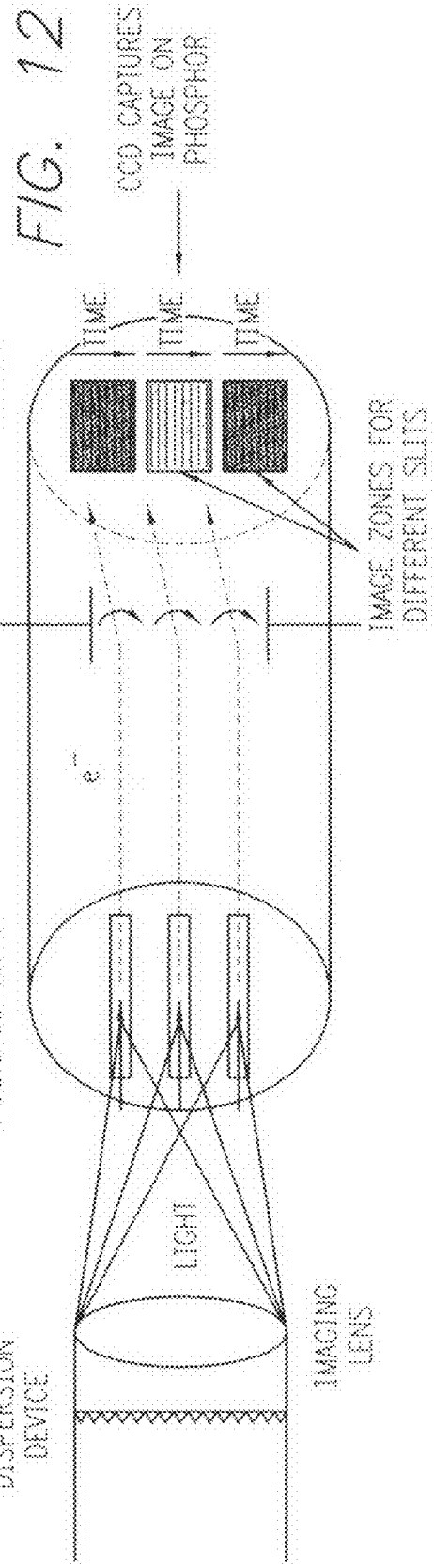

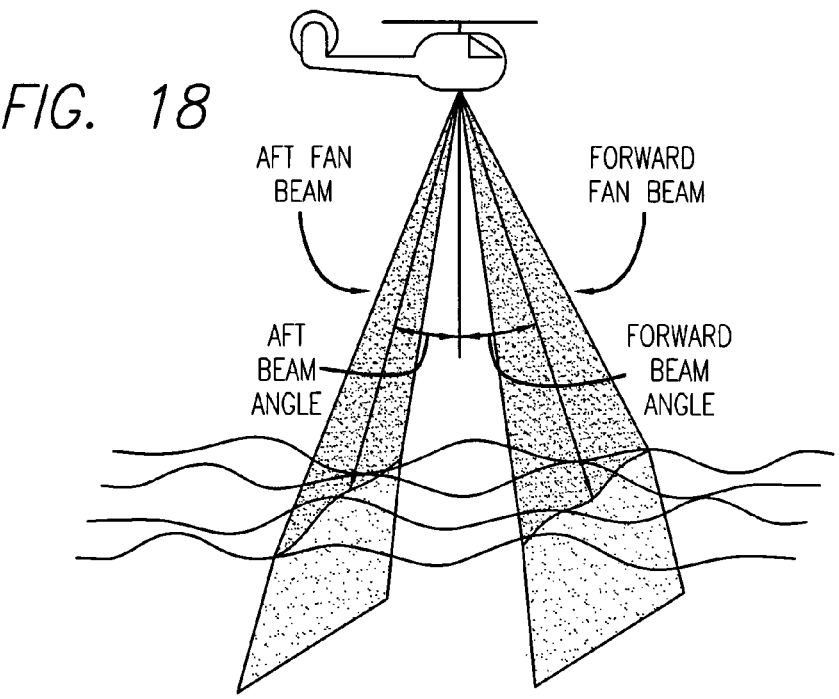
FIG. 18
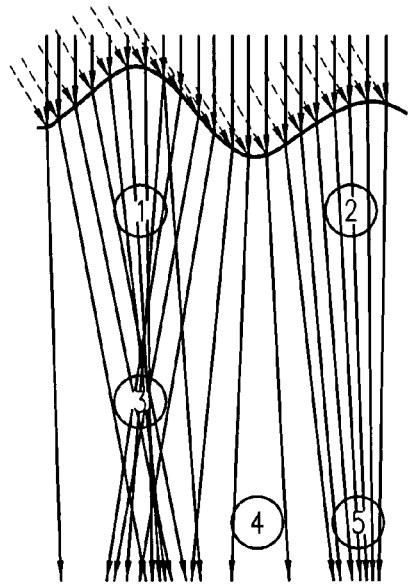
FIG. 19a
FIG. 19b
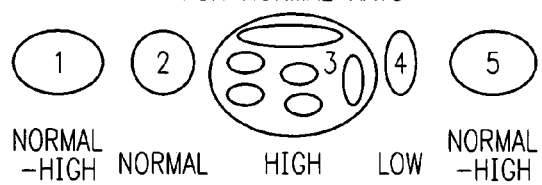
FIG. 19c
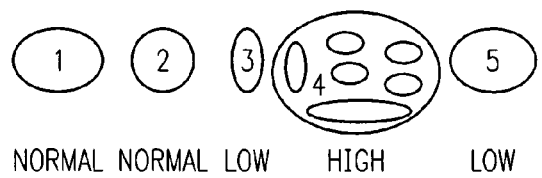

FIG. 21a
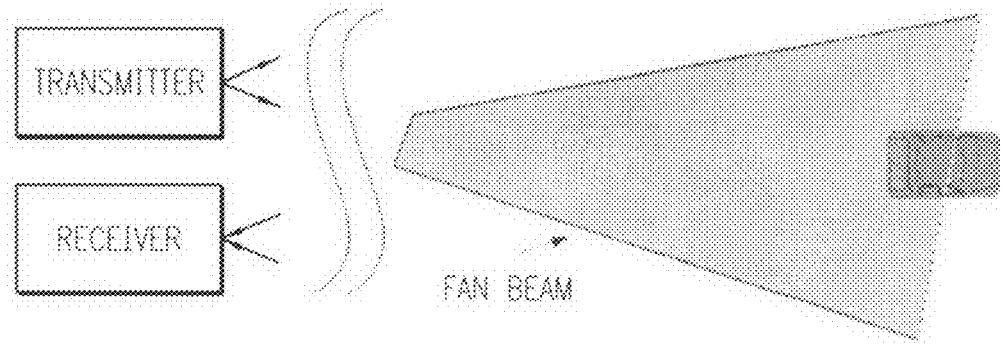
FIG. 21b
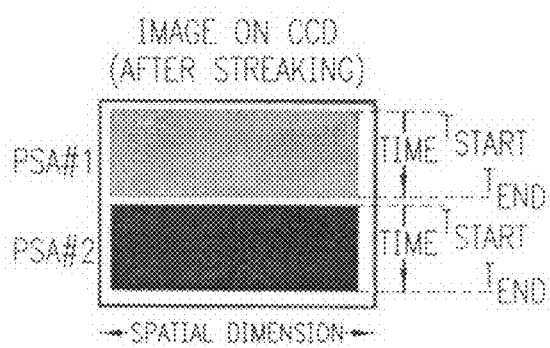
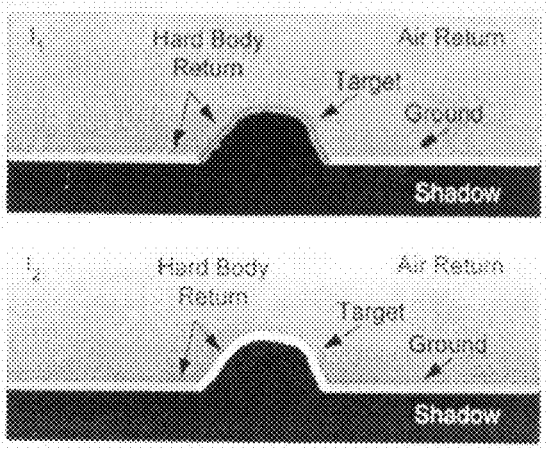
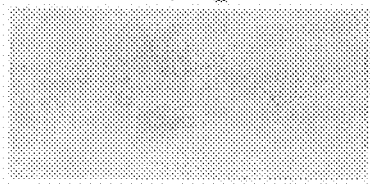
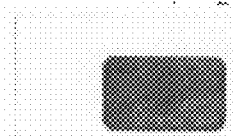
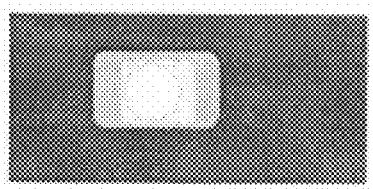
FIG. 21c

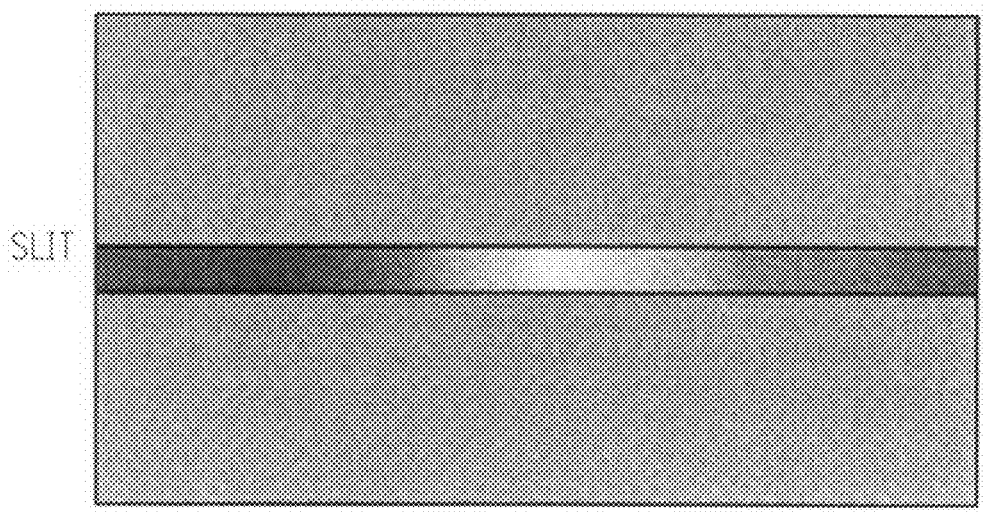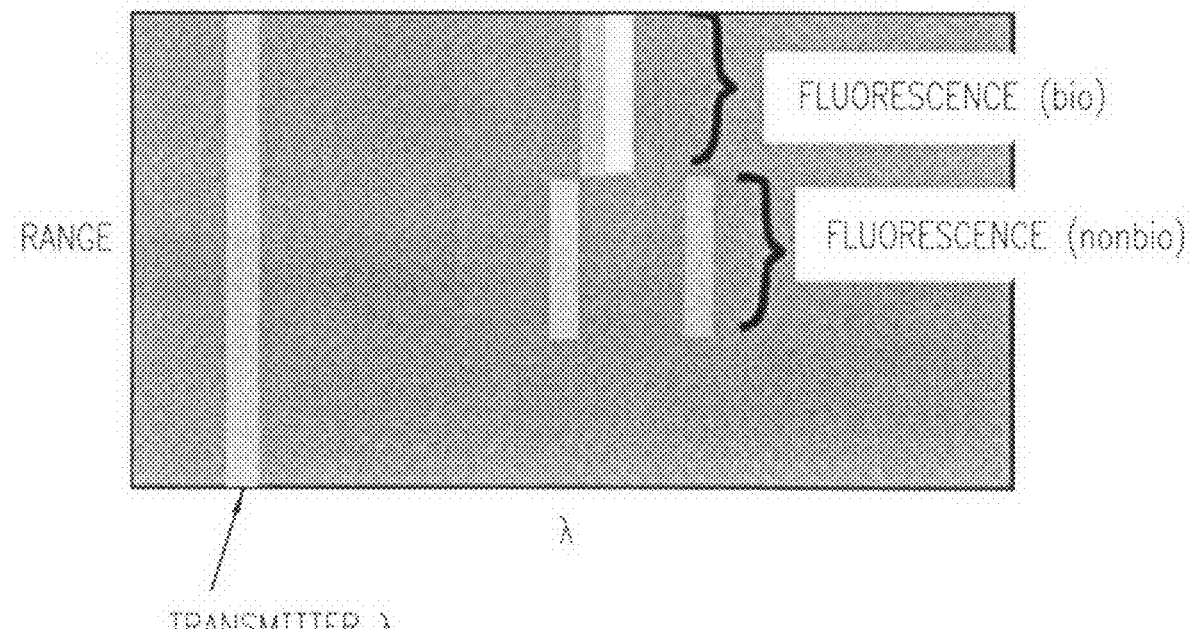
FIG. 24

VERY FAST TIME RESOLVED IMAGING IN MULTIPARAMETER MEASUREMENT SPACE HAVING MEANS FOR SEPARATING REFLECTED LIGHT TO FORM PLURAL BEAM IMAGES

This application is a divisional, and claims priority, of its parent U. S. nonprovisional application Ser. No. 10/258,917 filed Jun. 10, 2003 and issued Jun. 5, 2007 as U. S. Pat. No. 7,227,116; and further claims priority of its precursor international application, Serial PCT/US01/13489, filed Apr. 26, 2001; and in turn of its precursor U. S. provisional application, Ser. 60/199,915 filed Apr. 26, 2000.

BACKGROUND

1. Field of the Invention

This invention relates generally to time-resolved recording of three or more optical parameters simultaneously; and more particularly to novel methods and apparatus for making such measurements on an extremely short time scale, using lidar or a streak tube—or related technologies such as lenslet arrays—or combinations of these. Certain forms of the invention enable provision of a compact single-laser-pulse scannerless multidimensional imaging system using plural-slit streak-tube imaging lidar or "PSSTIL". The system is also capable of making plural-wavelength-band spectrally discriminating recordings of objects or phenomena, as well as plural-polarization-state recordings, and also combinations of such novel measurements.

2. Related Art (a) Conventional streak lidar—The term "lidar" (in English pronounced "LIE-dahr"), by analogy to "radar", means "light detection and ranging". The use of lidar is greatly enhanced by incorporating a streak tube—an electrooptical system for time resolving lidar returns to a remarkably fine degree.

Several advanced forms of the streak-tube imaging lidar or "STIL" technology are presented in other patent documents. See, for example, U.S. Pat. No. 5,467,122 and PCT publication WO 98/10372.

BENEFITS: Many strengths of a conventional STIL system appear in Table 1, and most of these are discussed in more detail in this section. This technology has demonstrated the capability to collect range (or other time-related) information with dynamic range and bandwidth that cannot be achieved using earlier conventional signal-digitization electronics.

TABLE 1

| Feature | Benefit |
|---|---|
| | Benefits of the conventional streak-tube imaging lidar (STIL) approach. |
| 12-bit linear dynamic range | Allows robust operations in high-contrast scenes. User need not spend time keeping system "centered" in the dynamic range. No electronic digitization can achieve this without significant compression (use of a logarithmic amplifier) that introduces artifacts in data. |
| Controllable range-operation from d. c. to multiGHz | Can change digitization rate "on the fly", which allows the operator to start out with coarse range resolution and "zoom" in on areas of interest. 1 cm range resolution has been demonstrated at short ranges; 15 cm, from an aircraft. Conventional high-speed digitization electronics are designed for only one speed. |
| Fast data collection | STIL operates on a single short-pulse (<10 nsec) time-of-flight measurement; thus no long integration or multiple pulsing is necessary. |

TABLE 1-continued

| Feature | Benefit |
|---|---|
| | Benefits of the conventional streak-tube imaging lidar (STIL) approach. |
| Compact ruggedized package | No target distortion/blur from moving source or target. The volume of commercial streak-tube electronics packaging has been reduced by a factor of twenty. Ruggedized hardware for helicopter environment has been fabricated. System can be placed on a variety of platforms. |
| High internal gain | The streak tube has a noiseless gain (noise factor is ~1) due to each accelerated photoelectron generating approximately three hundred photons on the phosphor screen. Higher gain (>$10^4$) available using a microchannel plate (MCP) if necessary. Raises small signals above the amplifier noise. |
| Simultaneous range and contrast images | No need for multiple sensors. Allows significant improvements to ATR algorithms for shape matching and for clutter reduction. No registration/scale issues between range and contrast data. |
| High frame rates shown | Transmitters and receivers have been demonstrated at 400 Hz frame rates-ideal for large-area searching. Ideal for very fast moving targets or sensors. |
| Rapid processing | All processing within a single image frame is conventionally performed with multiple DSP computers. Allows rapid real-time display for an operator. Reduces volume and electrical power requirements for computer. |

For example, linear twelve-bit dynamic range has been shown at controllable bandwidths up to and beyond 3 GHz. A fundamental advantage of a streak-tube-based lidar system is that it can provide hundreds or even thousands of channels of sampling at more than 3 GHz, with true twelve-bit dynamic range.

Such a receiver system provides range sample "bins" (i.e. discrete range-sampling intervals) that can be as small as five centimeters (two inches) long, and provides 4096 levels of grayscale imagery, both of which are important for robust operations. The small range bins provide optimal ranging capability, and the large dynamic range reduces the effort of trying to keep the scene illumination in the middle of the response curve of a limited-dynamic-range receiver. Such performance has been demonstrated in a laser radar configuration (J. McLean, "High Resolution 3-D Underwater Imaging", *Proc. SPIE* 3761, 1999).

BASIC TUBE ARCHITECTURE AND OPERATION: A streak tube (FIG. 1) as conventionally built nowadays is very similar to a standard image-intensifier tube, in that it is an evacuated tube with a photocathode, producing electrons which are accelerated by very high voltages to a phosphor screen. In operation of a typical system, each such electron ejects roughly three hundred photons from the phosphor, which is then collected by an image-recording device such as a CCD.

A major difference is that a streak tube has an extra pair of plates that deflect an electron beam, somewhat as do the deflection plates in an ordinary cathode ray tube (CRT) tube used in most oscilloscopes, television sets and computer monitors. In conventional STIL operation, input photons are limited to a single slit-formed image—causing the electron beam within the tube to be slit-shaped.

A fast ramp voltage is applied to the deflection plates, very rapidly and continuously displacing or "streaking" the slit-shaped electron beam, parallel to its narrow dimension, from the top (as oriented in FIG. 1) of the phosphor screen to the bottom—effectively creating a series of line images formed at different times during the sweep. Thereby time information is impressed upon the screen image in the streak direction (here vertical), while spatial information is arrayed along the slit length.

The array of internal electronic line images in turn constitutes a latent areal image—which can be picked up ("developed") by phosphor on the screen. Most typically a charge-coupled-device (CCD) camera is attached to the streak tube to collect the image from the phosphor screen.

In this way the image is reconverted to an external electronic image by a CCD. The CCD output is digitized, interpreted, and if desired saved or displayed by receiving electronics.

One of the two dimensions of each two-dimensional image acquired in this way is azimuth (taking the dimension parallel to the long dimension of the slit as extending left and right)—just as with a common photographic or video camera. The other of the two dimensions, however, is unlike what an ordinary camera captures.

More specifically, the STIL images represent azimuth vs. range from the apparatus—not vs. the commonplace orthogonally visible dimension as with a common camera. Thus for example if a two-dimensional image of an ocean volume is acquired by an instrument pointed vertically downward into the sea, the two dimensions are azimuth and ocean depth.

The operation described here should not be confused with that of a so-called "framing camera", whose tube internal geometry is commonly identical but which usually lacks an optical input slit, and whose deflection system is differently energized—so that more ordinary two-dimensional images of a scene are formed at the phosphor screen. Often such images are sized to fit on just a fraction of the screen area, and the deflection plates quickly step the two-dimensional-image position (in some instruments during a blanking interval), rather than displacing it continuously as in streaking.

BASIC SYSTEM OPERATION: In a typical conventional streak-tube lidar configuration, a short-duration high-energy laser pulse is emitted. The emitted beam is spread out into a single thin, fan-shaped beam or line, which is directed toward a landscape, ocean volume, or other region of interest—and the receiver optics image the line back onto the slit input to the streak tube. (A later portion of this document discusses the phrase "thin, fan-shaped beam" in further detail.)

In such a standard STIL system, coverage of the region of interest in the dimension perpendicular to the line illumination (FIG. 2) is generally accomplished through motion of a vehicle carrying the emitter and sensor successive pulses of the beam. Formation of a complete volumetric image therefore requires a series of pulses, each yielding a respective individual range-vs.-azimuth image.

Taking the laser projection direction as horizontal in FIG. 2(a), the vehicle direction should be vertical—as for instance in a vertically moving helicopter. In this case, each areal screen image represents a horizontal map, at a respective altitude, with the measuring instrument located above the top edge of the map and the remote horizon along the bottom edge.

Alternatively, reverting to the earlier example of a downward-looking instrument over the ocean, vehicle motion should be horizontal. In this case each areal screen image represents a vertical slice of the ocean below the vehicle, at a respective position along the vehicle's horizontal path.

This is sometimes familiarly called a "pushbroom" system. A demonstrated alternative to vehicle-based data acquisition is a one-dimensional scanner system used from a fixed platform.

The deflection system of the streak tube is set to streak the electron beam completely down the phosphor screen in some specific time, called the "sweep time" of the tube. This also corresponds to the total range gate time (i.e., the total amount of time during which the system digitizes range data).

Ordinarily the sweep time is adjusted to fully display some interval of interest for exploring a particular region, as for instance some specific ocean depth from which useful beam return can be obtained—taking into account turbidity of the water. The starting point of the range gate is controlled by the trigger signal used to begin the sweep.

Computer control of both the sweep time and the sweep-start trigger provides the operator a flexible lidar system that can very rapidly change its range-gate size, its range-digitization starting point, and also its range-sampling resolution. This enables the system to search large areas of range with coarse range resolution, and then "zoom in" to obtain a high-resolution image around a discovered region of particular interest. For example, in one pulse the system could capture a range from 5 km to 7 km at low resolution, and then on the next laser pulse zoom in to 6 km±50 m and thereby image an object of prospective interest at the highest resolution.

Each column of CCD pixels corresponds to one channel of digitized range data, such as would be collected from a single time-resolved detector—for instance a photomultiplier tube (PMT) or an avalanche photodiode (APD). Each row is the slit image at a different time.

The size (in units of time) of the previously mentioned range bins is simply the sweep time divided by the number of pixels in the CCD columns. Such values are readily converted into distance units through multiplication by the speed of light in the relevant medium or media.

MODERN-DAY ENHANCEMENTS: Considerable practical advancement is now available in state-of-the-art streak-tube technology. Such advances include a compact ruggedized package suitable for helicopter environment.

Such a unit (FIG. 3) is only about 15 cm (6 inches) wide, 47 cm (19 inches) long, and 37 cm (15 inches) in diameter. This kind of device has complete computer control of all streak-tube parameters, including high-voltage supplies.

Available as well are continuously variable linear sweep speeds from 50 nsec to 2 μsec. High-speed tube gating without a microchannel plate (MCP) is also offered, for enhanced signal-to-noise ratio.

ADVANCED COMMERCIAL FORM: The assignee of this patent document, Aret é Associates (of Sherman Oaks, Calif., and Tucson, Ariz.), has developed an airborne STIL system for bathymetry and terrestrial mapping. This device contains a diode-pumped solid-state Nd:YAG laser that is frequency doubled to 532 nm. This wavelength was chosen for maximum water penetration for the bathymetry task and for proximity to the peak of the streak-tube photocathode responsivity curve.

A raw image frame taken by STIL during airborne terrestrial mapping data collection (FIG. 4[b]) and a volume reconstruction from numerous such frames (FIG. 4[c]) compare interestingly with a conventional photograph (FIG. 4[a]). A like comparison is also shown (FIG. 5) for an object roughly 1 m (39 inches) in diameter and imaged through 6 m (20 feet) of seawater.

In these views, naturally the conventional photo gives a clearer and sharper image. One goal of the STIL imaging, however, is to obtain images and reconstructions under circumstances that preclude effective use of ordinary photos.

Of particular interest in view (c) is the dark spot in the upper-left part of the imaged object: this is one of the two 5 cm (two inch) holes in the object that appear in view (a). Here the STIL system is actually ranging down through that hole to the bottom of the object. (The other hole was covered by a weight used to keep the object on the ocean bottom.)

As the scattering and attenuation of water are significantly greater (and propagation velocity significantly smaller) than in air, Areté has developed and tested the algorithms and software to account for such problems. These algorithms are directly translatable to long-range air paths, and propagation through fog, haze, smoke etc.

(b) Safety limitations of conventional lidar—Modern STIL innovations were developed for underwater applications that require blue-green light for optimal water penetration. Human beings too are particularly adapted for sensitivity to light in these wavelengths.

By the same token, however, such light when projected at very high powers can pose a hazard to people—and possibly to other creatures as well—who may be positioned to look directly at the source. The possible hazard is compounded by a like sensitivity to viewing specular reflections of the beam from the source.

As will be understood, the STIL system has many useful applications in which this type of potential hazard poses no significant concern. A thrust of the present document, however, is development of a new generation of STIL systems and applications that are industrial and even commercial, and accordingly introduce a much greater need for compatibility with the population at large.

Therefore the possibility of injury to eyes is an important obstacle to a new array of STIL devices. It may be in part due to this problem that widespread commercial and industrial adaptations of the STIL principle have failed to appear in the marketplace.

(c) Conventional lidar streak-unit limitations—As the preceding introductory sections suggest, conventional modern streak tubes are relatively sizable vacuum tubes that use high voltages to streak the electron beam generated from the photocathode. Plainly this type of hardware is subject to several drawbacks.

Such devices are very expensive to make, maintain and use. For field use, ruggedization is a necessary added expense (and a still-imperfect solution) since large vacuum tubes are inherently somewhat fragile. Their external high-tension connections are not optimal for routine use in aircraft.

A well-known alternative is optical streaking—in which a beam of incoming photons is rapidly displaced across a detector, along the range axis, entirely avoiding the need for a vacuum tube. This in fact was the earliest form of the streak camera—using a fast scan mirror, in particular a large spinning polygon (FIG. 11 [a]).

These devices too, unfortunately, are problematic and even more so than the electronic form. The drawback of this approach as conventionally implemented is the requirement for the large high-speed rotating mirror, which is both bulky and relatively delicate. (One relatively modern example of such an installation is described by Ching C. Lai in "A New Tubeless Nanosecond Streak Camera Based on Optical Deflection and Direct CCD Imaging,", *Proc. SPIE* vol. 1801, 1992, pp. 454-69.)

What makes these drawbacks of the optical streaking technique particularly unfortunate is that streaking with an optical device would otherwise greatly expand the choices in commonly available detectors. It would allow the use of common detectors for the wavelengths of interest—e.g. silicon CCD and CMOS detectors for the visible and near IR, and HgCdTe, PtSi, or InSb arrays for the longer IR, out to 11-micron wavelengths if desired.

Longer-wavelength operation would be advantageous for various special applications. These include better penetration of fog, clouds and some types of smoke; and also enhanced discrimination of object types by their different reflectivities at corresponding different wavelengths.

Regrettably the common detectors just mentioned are not suited for use as photocathode materials, to generate electrons that can then be streaked inside a streak tube. On the other hand it would accomplish nothing to place them following the conventional photocathode—e.g. at the streak-tube anode—since conversion from the optical to the electronic domain has already been accomplished at the cathode.

Use of a standard IR imaging detector instead of a CCD would be advantageous to provide high-quantum-efficiency images. For some wavelength ranges this technique would be ideal—but the prior art has avoided these potential solutions because of the recognized problems presented by spinning mirrors.

(d) Conventional lidar imaging limitations—As a general observation, conceptually a STIL system is far in advance of competing technologies in terms of resolution capability in three dimensions, and in terms of signal-to-noise ratio as well. In its ability to fully exploit these advantages, however, a conventional STIL is severely impaired by an overriding problem in streak lidar systems heretofore: inflexibility of pixel allocation.

This limitation may be appreciated from three different perspectives, although in a sense they are only different aspects of the common phenomenon:

the STIL cannot record in three dimensions without mechanical movement of the measuring instrument relative to the region to be inspected;

the only practical way to make optimally efficient use of the very expensive detector area in a conventional STIL system is to build a fiber-optic remapper; and even when such a device has been built, a conventional STIL system fails to make fully economic use of that investment.

These problems will be taken up in turn below, but first beginning with a demonstration of the above preliminary observation that 3-D resolution is superior in a STIL apparatus.

THREE-DIMENSIONAL RESOLUTION: Different existing lidar systems sample a water volume differently (FIG. 16). The water surface is represented by the irregular line shown on the two visible faces of the volume cube, in each view.

Range-gated systems have excellent transverse spatial resolution, but only have one range pixel per camera—which results in poor range resolution as suggested by the relatively tall volume elements (FIG. 16[a]) in the shaded zone that is of interest. Merely by way of example, one system well-known in this field as "Magic Lantern" is forced to use six separate cameras to cover multiple depths, resulting in a large and expensive system.

In addition, since a range-gated system thus collects large vertical sections of the water column, contrast of any object images is significantly reduced. That is, the contrast, which is directly proportional to the signal-to-noise ratio (SNR) in the region, is a function of the amount of water backscatter that is collected.

A system with range samples of 30 cm (one foot) has ten times the SNR of a system that has 3 m (ten foot) range samples. In addition, as the diagram also suggests, the range-gated device must avoid the surface of the water.

Time-resolved systems, such as the one used in the advanced receiver in ATD-111 (a photomultiplier-tube-based, nonstreaking time-resolved lidar system), suffer from a similar contrast-reduction problem. In this case the cause is poor transverse spatial resolution, as suggested by the relatively broad volume elements (FIG. 16[$b$]) in the shaded zone of interest.

This system cannot isolate an object signal, and moreover also collects a large area of water backscatter around an object. To have the same transverse spatial resolution as the range-gated system, this time-resolved apparatus would require a separate laser pulse for every pixel, resulting in a pulse repetition frequency (PRF) exceeding 100 kHz.

Unfortunately a frequency-doubled Q-switched Nd:YAG laser (the primary laser used in ocean lidar systems) operates efficiently only up to about 5 kHz. Inability to reach the needed PRF, in turn, results in larger spatial pixels to achieve the same area coverage.

To avoid these sampling problems, the two systems discussed above use both a time-resolved receiver and a range-gated module. Although this approach represents significant additional system complexity, it still does not resolve the significant degradation of detection SNR.

Because a STIL system collects 500 to 1000 spatial pixels per laser pulse, the PRF can be in the hundreds of hertz, which is well within the performance envelope of the Nd:YAG lasers. In this way a STIL device can achieve pixel sizes smaller than an object of interest; therefore, it has higher SNR for the same laser power.

Thus, a streak-tube-based system (FIG. 16[$c$]) can provide much higher SNR for the same amount of laser power, or can achieve equal performance with a significantly smaller laser system. Streak-tube-based systems can provide good resolution in all dimensions.

Unfortunately this powerful benefit of the STIL principle is not heretofore broadly available without mechanical movement of the detector, and without costly and awkward remapping devices—and even then carries only very limited amounts of image information. These three problems are discussed in the paragraphs below.

THE MECHANICAL-MOVEMENT REQUIREMENT: As described earlier, the conventional streak-tube system is a pushbroom system, which means that it depends on the motion of the vehicle to sample the dimension along the track. This requirement prevents the conventional STIL from serving as what may be called a "staring" system—i.e., a stationary system that can acquire a stationary image of an area.

Just such a capability, however, is quite desirable for a number of useful applications. Inability of a conventional STIL instrument to fill this role is a major limitation in industrial and commercial uses.

FIBER-OPTIC REMAPPERS—CHARACTER AND COST: It is well known to use a variety of kinds of fiber-optic units to reconfigure a time-varying area image as a line image, and thereby enable time resolution of the changing content in the area image. Such technologies are seen in representative patents of Alfano (for example see U.S. Pat. No. 5,142,372), and of Knight (for example U.S. Re. 33,865); and in their technical papers as well.

An original concept for an area-image streak-tube system was demonstrated by Knight, who mapped a 16×16-unit areal image onto a conventional streak-tube slit, with fiber optics. (F. K. Knight, et al., "Three dimensional imaging using a single laser pulse", *Proc. SPIE* vol. 1103, 1989, pp. 174-89.) This technique was severely limited in overall number of spatial pixels because of the relatively small number of pixels that can be mapped onto a slit.

Low-resolution fiber image redistribution (a 16×16 focal plane to a single 256-pixel line) has also been performed for streak tubes by MIT-Lincoln Labs. Many fiber-array manufacturers are in operation and ready to prepare units suited for STIL work: one of the largest firms is INCOM; another that makes individual fiber arrays is Polymicro Technologies—which has previously prepared arrays with 3000 fibers.

At best, however, all such approaches are hampered by the costly custom fabrication required, and the need to manufacture a special unit for each desired mapping respectively.

FIBER-OPTIC REMAPPERS—INADEQUATE EXPLOITATION: What makes matters worse, as to fiber-optic remapping, is that a conventional STIL system nowadays continues to face the same basic obstacle seen in the Knight paper noted above. Only so many original image pixels can be meaningfully rearranged onto a slit.

This means that even after the limitation of expensive custom fabrication has been confronted and in a sense overcome by a decision to expend the necessary funds, and even after the requirement for making a separate special unit for each of several particular mappings has also been faced and in a sense overcome by a decision to invest even that multiple—yet nevertheless the technology continues to be not only uneconomic but also technically unsatisfactory because the resulting images carry inadequate, frustratingly small amounts of image information. This obstacle has heretofore remained a persistent problem, and will be further discussed shortly in subsections (f) and (g).

(e) WFS limitations of conventional lidar—The field of wavefront sensors (WFS) is an important one for laser diagnostics. High-power short-pulse lasers are essential components of several different applications (e.g., laser trackers and imaging laser radar); however, such lasers are notoriously unreliable.

It is difficult for vendors to manufacture them to desired specifications, and the devices seldom survive to their projected lifetime (at least at rated output power). One of the most difficult aspects of the manufacture of such devices is the lack of diagnostic equipment for the total characterization of the laser output.

Typical laboratory equipment for the characterization of high-power pulsed lasers consists of three instruments: (1) a power meter for measuring average power, (2) a single fast detector with an oscilloscope for measuring the pulse width temporally, and (3) a laser characterization imager that provides a spatial display of the beam intensity. Each of these instruments has significant limitations in the data that it produces.

The single fast detector averages over the spatial components of the beam, and the laser characterization imager averages over the temporal component of the beam. That is to say, the integration time of the camera in the laser characterization setup is typically orders of magnitude longer than the laser pulse width.

The power detector, furthermore, averages over both the spatial component and the temporal component. Thus no one instrument provides information in time and space and phase with high resolution in all dimensions.

Yet this is precisely the information that the laser designers use in their modeling and simulations. Using commercial laser modeling software such as GLAD, laser designers set up models to simulate propagation of the beam in the laser cavity at very high spatial and temporal resolution.

The phase and intensity of the light, expressed as electric fields, are used in this simulated propagation process. After going through all of that analysis, however, laser designers have no way to compare the actually resulting, operating product with that preliminary analysis.

None of the above-discussed three instruments measures the wavefront of the light—i.e., maps the phase of the outgoing light as a function of position in the beam. This is the role of another type of instrument, the WFS, which does exist to perform this task—but like the laser characterization imager it averages over time.

The most common such unit in use today is the Hartmann-Shack WFS. In this apparatus, incoming light (FIG. 25) is split up into multiple subapertures, each with its own lenslet. The lenslet focuses the light onto a detector.

When a flat wavefront (i.e., a plane wave) is incident on the device, each of the lenslets forms a spot image on-axis on the detector. When a distorted wavefront arrives, however, as illustrated the average slope of the wavefront at the lenslet for each subaperture displaces the spot away from the on-axis position.

Although the illustration is essentially one-dimensional, the lenslets are in a two-dimensional array; and the spot position measurements too are accordingly made in two dimensions. Design and fabrication of this kind of device is a highly specialized endeavor, available from various vendors such as Wavefront Sciences, Inc. of Albuquerque, N. Mex.

Wavefront Sciences develops lenslet arrays for a number of applications. Typical cost for initial design and fabrication of one lenslet array is $20,000.

The displacement of the spot is measured, in both the x and y directions. Average local slope of the wavefront at the measurement point is next calculated as linearly proportional to this displacement. The total wavefront is then reconstructed using algorithms that assemble such local tilts into a whole wavefront.

This process is referred to as "wavefront reconstruction". It is a common and well-documented algorithm, currently used in astronomical and many other instruments.

In addition to the wavefront, which corresponds to the phase of the electric field, the intensity of the light is measured for each subaperture. This allows generation of an intensity map, as well as a phase map, of the incoming beam.

In most Hartmann-Shack WFS units, the detector behind the optics is a CCD camera or an array of quad cells. A quad cell (FIG. 26) measures the two tilts and the intensity. These detector systems are relatively slow (30 Hz to 10 kHz); while sufficient for assessing atmospheric corrections such detection naturally is inadequate for applications that require sub-nanosecond sample rates.

From the foregoing it will be clear that laser laboratory devices, and in particular WFS systems when used for laser evaluation, fail to satisfy the needs of laser developers. This failure is a major problem, impeding progress in the design and refinement of more stable, reliable and long-lived lasers.

(f) Data-speed and package limitations—Signal processing in conventional STIL systems is performed using multiple digital signal processors (DSPs). These in turn impose requirements of weight, volume, power, and heat-loading which in effect demand vehicle-mounting of these sensors.

Even carried on a vehicle of modest size, practical forms of the system have relatively low data throughput and may therefore require several measurement passes to acquire adequate data for a region of interest. These limitations represent additional problems because many applications would be better served by a system that a single person could carry, or that could survey and map a region in a single pass—or ideally both.

(g) Limited uses of conventional streak lidar—No STIL packages fully suited for commercial or industrial surveillance and mapping are known to be on the market. It appears that this may be due to a combination of factors including the visual hazards mentioned earlier (with the legal liability that would be associated with operations in populated areas), and also the limited data speed and resulting packaging obstacles outlined just above.

Potentially, a primary commercial application is airborne three-dimensional terrain mapping. Terrestrial mapping is one function that can be performed using lidar, but this opportunity has not been exploited commercially. It is believed that this market may represent potential income exceeding tens of millions of dollars annually.

In California, for example, there is a need to perform complete surveys of the Los Angeles basin (2,400 square miles) every year. This task is currently performed using photogrammetry techniques. Other metropolitan areas have similar requirements, which in the aggregate thus can provide a sustained business in airborne surveying.

An entree to this terrestrial mapping application can be obtained by contacting any large commercial and industrial surveying company. A very roughly equal amount of business can be generated through "on demand" surveying for particular construction jobs—particularly three-dimensional imaging.

Conventional STIL equipment, however, has not been set up (or at least not set up in a convenient format) for three-dimensional imaging. Likewise it is not available with any kind of viewing redundancy, to surmount problems of temporary or local barriers to viewing.

On land such barriers include for example landscaping or natural forestation, as well as coverings deliberately placed over some objects. At sea they include image-distorting effects of ocean waves (FIG. 19)—which may completely obscure some features and actually exchange the apparent positions of others.

In purest principle it is known that foliage and other kinds of cover can be neutralized through use of spectral signatures, polarization signatures or fluorescence signatures. Analysis that incorporates spectral, polarization, spectropolarization, and fluorescence discriminations is also known to be useful for other forms of optical monitoring for which streak lidar would be extremely well suited.

Significant analysis of three-dimensional polarization analysis with lidar systems, using a "Mueller matrix" approach, is in the technical literature. See, for example, A. D. Gleckler, A. Gelbart, J. M. Bowden, "Multispectral and hyperspectral 3D imaging lidar based upon the multiple slit streak tube imaging lidar", *Proc. SPIE* vol. 4377, April 2001; A. D. Gleckler, A. Gelbart, "Three-dimensional imaging polarimetry", *Proc. SPIE* vol. 4377, April 2001; A. D. Gleckler, "Multiple-Slit Streak Tube Imaging Lidar (MS-STIL) Applications," *Proc. SPIE* vol. 4035, p. 266-278, 2000; R. M. A. Azzam and N. M. Bashara, *Ellipsometry and Polarized Light*, North Holland, Amsterdam (1977); R. A. Chipman, E. A. Sornsin, and J. L. Pezzaniti, "Mueller matrix imaging polarimetry: An overview" in Polarization Analysis and Applications to Device Technology, SPIE Volume 2873, June 1996; R. M. A. Azzam, "Mueller matrix ellipsometry: a review", SPIE Volume 3121, August 1997; P. Elies, et al., Surface rugosity and polarimetric analysis, SPIE Volume 2782, September 1996; Shih-Yau Lu & R. A. Chipman, Interpretation of Mueller matrices based on polar decomposition, JOSA, Volume 13, No. 5, May 1996; and S. Breugnot and P. Clemenceau, "Modeling and performance of a polarization active imager at $\lambda=806$ nm", SPIE Vol. 3707, April 1999.

Thus spectral, fluorescence and polarization analyses in theory are susceptible to commercial and industrial streak-lidar beneficial exploitation. Examples are detection and measurement of atmospheric particulates, atmospheric constituents, waterborne particulates, and certain hard-body object returns (with propagation paths in either air or water).

Heretofore, however, necessary equipment adaptations for introducing fluorescence, polarization and spectral analyses into streak lidar work—at least on a broad, general-use basis—have been unavailable. The prior art in this field thus fails to teach how to go about making such refinements in any straightforward, practical way. This gap represents a major problem as it has left these kinds of mapping infeasible or even impossible—and accordingly several practical mapping needs unsolved.

(h) Now-unrelated technology: "eye safe"—This discussion will next turn to modern developments that have not heretofore been pragmatically associated with lidar, or particularly with streak imaging lidar. The first of these relates to population exposure.

Studies have shown that light beams of different wavelengths have respective ocular destructive powers—for any given beam power—that differ by many orders of magnitude. For all wavelengths, such studies have established respective maximum power/pulse-energy levels that are considered safe, at least for humans.

In particular the 1.5-micron region is considered to have the least ocular destructive power (by several orders of magnitude) of any wavelength from x-rays to the far infrared. More specifically, light in the visible, near-UV, and near-IR regions damages the retina, while light in the far-UV and far-IR damages the cornea; but light at about 1.5 microns tends to dissipate harmlessly in the intraocular fluid between the cornea and the retina. This region is therefore commonly designated "eye safe".

Accordingly for mapping or detecting systems that are to irradiate large areas of land in which people or other higher organisms may be present, it is important to operate in that eye-safe wavelength region as much as possible. Of course there are many reasons to avoid incidental exposure of people above the damage threshold.

Traditional photocathode materials are well suited at visible wavelengths; however, efficient photocathode detector materials do not exist for wavelengths much over one micron. Nevertheless operation at eye-safe wavelengths is feasible with commercially available fast phosphorescent materials, which respond to infrared photons by producing proportional quantities of higher-frequency (visible) photons, and are thus loosely described as performing wavelength "conversion".

These materials thus in effect "convert" light at 1.5 microns to roughly 0.65 micron, with quantum efficiencies potentially as high as sixty-six percent. This process, sometimes called "upconversion" to visible light, occurs at the front of an imaging tube—in advance of the photocathode—and enables use of conventional photocathode materials that respond well to visible light.

TRANSMITTER: Transmitters operating at 1.5 microns are now commonly available from several vendors (including Big Sky Laser, LiteCycles, and GEC-Marconi) using diode-pumped solid state (DPSS) Q-switched Nd:YAG lasers. The lasers are coupled with either an optical parametric oscillator (OPO) or a stimulated Raman scattering (SRS) cell.

To achieve optimal range resolution, it is desired to keep the laser pulse length between 4 and 10 nsec. This is the range of typical DPSS Q-switched pulse lengths; accordingly transmitter conversion is straightforward within the state of the art.

RECEIVER: Streak-camera receiver operation at 1.5 microns is currently available using the standard S1 photocathode material. Unfortunately, S1 has very poor quantum efficiency, which reduces the applicability for real-world imaging.

Due to the low efficiency of the S1 material, a 1.5-micron streak-lidar product based upon it would similarly operate inefficiently. Pragmatically speaking, such a product would not be economic or viable.

Exploration of other materials has been reported. Those materials which are relevant to vacuum streak-tube operation include:
  TE photocathode,
  InGaAs photocathode,
  ETIR upconversion, and
  nonlinear upconversion.

These will be discussed in turn below, in this subsection of the present document. Another approach to eye-safe technology, but that excludes vacuum streak-tube operation entirely, will be discussed in a later subsection.

TE Photocathode: Intevac Corp. has fabricated a transfer-electron (TE) photocathode with quantum efficiencies exceeding ten percent at 1.5 micron wavelengths. (See K. Costello, V. Abbe, et al., "Transferred electron photocathode with greater than 20% quantum efficiency beyond 1 micron", *Proc. SPIE* vol. 2550, pp. 177-88, 1995.) This photocathode has been demonstrated in image-intensified CCDs—but not in streak tubes—at 1.5 microns.

Very interestingly, applicability of the TE photocathode for streak tubes has been shown too, but not at that eye-safe wavelength. (Please refer to V. W. Abbe, K. Costello, G. Davis, R. Weiss, "Photocathode development for a 1300 nm streak tube", *Proc. SPIE* vol. 2022, 1993.)

Intevac used an early version of this photocathode in a streak tube that operated out to 1.3 microns—but, again, not to 1.5. Whether actually due to perceived lack of customer base or due to some failure in reduction to practice, no streak tube able to operate efficiently at 1.5 microns is currently available.

InGaAs Photocathode: Hamamatsu Corporation of Japan has an InGaAs photocathode used for near-IR photomultiplier tubes (PMTs). The Hamamatsu photocathode has poorer quantum efficiency (QE)—on the order of one percent—at 1.5 microns than the TE discussed above.

Although Hamamatsu suggests that this photocathode as compatible with its streak-tube line, no such development has appeared, at least commercially or in the literature. Again, pragmatically no successful report of testing is known.

Improvements in QE may be possible if "slower" photocathodes that have a longer response time—1 nsec, vs. tens of picoseconds—are acceptable. Nanosecond response time at the photocathode would have little adverse impact on system performance.

ETIR Phosphor Upconversion: Phosphor upconversion has been performed by simply placing a layer of phosphor in front of a photocathode, in image intensifiers and other photoresponsive devices. No testing with a streak-tube photocathode, however, has been reported.

In known applications of the phosphor-upconversion technique, the incoming IR interacts with the phosphor, which has been "charged" with blue light from an LED, and in response produces light between 600 and 700 nm. This is well within the high-performance range of conventional photocathode materials. The blue charging LED can be shut off during the brief data-collection period to avoid saturating the photocathode.

This technique is particularly effective using a class of phosphors, called "electron-trapping infrared" (ETIR) upconversion phosphors, which receive incident infrared photons and in response emit corresponding quantities of visible photons.

The response band of typical ETIR phosphors is about 0.8 to 1.6 µm. The most accepted model for the operation of ETIR phosphors is as follows.

(1) The phosphors are doped such that there are two doping levels between the valence and conduction bands, with the lower doping level called the "trapping level" and the upper doping level called the "communication level".

(2) Visible photons (typically blue to green) excite electrons from the ground state to levels higher than the trapping level.

(3) In the combination process, most electrons then fall to the trapping level where they can remain for very protracted time periods (years), in the absence of infrared photons with energies corresponding to the gap between the trapping and communication level.

(4) Incident infrared photons excite the electrons in the trapping level to the communication level, where they radiatively decay to the ground state by combining with holes in the ground state—releasing visible photons (typically orange to red).

Another class of infrared upconversion phosphors is antiStokes (AS) phosphors. Since these phosphors operate via a multiphoton process, they have higher thresholds and lower conversion efficiencies than do the ETIR phosphors. AS phosphors, however, do not require visible pump photons for operation as do the ETIR phosphors. The need for a visible pump is not a major drawback for the ETIR phosphors, since the pump need not be coherent—and hence LEDs can be used as the pump source.

Nonlinear optical processes competing with ETIR phosphors include second harmonic generation (SHG), stimulated Raman scattering (SRS) antiStokes (AS) lines, and sum-frequency generation. The ETIR phosphors have an advantage over all these competitors, namely that there are no phase matching or coherency requirements, so that the ETIR process can operate over the wide incidence angles required for imaging.

Commercially available ETIR films from Lumitek International, Inc. (formerly Quantex) have been reported with 2 nsec pulse response width and twenty-two percent quantum efficiency (in reflective mode), from 1.06 µm to visible for the company's Q-11-R film. (Ping, Gong and Hou Xun, "A New Material Applicable in the Infrared Streak Camera," *Chinese Journal of Infrared and Millimeter Waves*, vol. 14, No. 2, 1996, pp. 181-82.)

Quantex has developed a near-infrared image intensifier (model I2) using an ETIR phosphor screen. In this project the company measured the minimum sensitivity—at several wavelengths—of a thick-film phosphor screen mated with the image intensifier in transmissive mode. (Lindmayer, Joseph and David McGuire, "An Extended Range Near-Infrared Image Intensifier," Electron Tubes and Image Intensifiers, [ed.] Illes P. Csorba, *Proc. SPIE* vol. 1243, 1990, pp. 107-13.)

Measured minimum sensitivity of this phosphor-I2 sensor at 1.55 µm was 670 nW/cm$^2$ (ibid. at 108). Quantex had also vapor-deposited thin films of the ETIR material onto an image-intensifier fiber-optic faceplate to improve the imaging resolution. The resolution obtained with this device was 36 line-pairs/mm, corresponding to the resolution of the 15 µm fiber pitch of the faceplate.

Researchers at Xi'an Institute of Optics and Precision Mechanics, Chinese Academy of Sciences, have reported the development of faster, more efficient ETIR phosphors. (Ping, Gong and Hou Xun, loc. cit.)

They reported a red-emitting and a blue-emitting ETIR phosphor—the red phosphor having a 1.3 nsec response width and a 66% quantum efficiency in transmissive mode, and the blue phosphor having a 1.4 nsec response width and a 47% quantum efficiency in transmissive mode.

Nonlinear upconversion: Because conversion efficiency is a function of optical power, nonlinear upconversion techniques such as SHG and SRS are not practical for low-level signals. Consequently, these techniques are typically used with the transmitter rather than the receiver.

Also, because of phase matching requirements these techniques are typically only efficient over limited fields of view. There is a technique in which the signal can be amplified optically in a Raman crystal, to allow for efficient upconversion—or to directly overcome the poor quantum efficiency of an S1 photocathode (Calmes, Lonnie C., et al., "Marine Raman Image Amplification", Proc. SPIE Vol. 3761, 1999). At present a drawback of this technique, with respect to long-range streak-tube operations, is that the Raman amplifier can be pulsed on for only 10 to 15 nsec at a time.

As to operation at longer wavelengths (1.6 to 10 microns), advantageous for various specialized applications as mentioned earlier, Quantex has also reported ETIR phosphors for upconverting medium-wavelength infrared (3.1 to 4.5 µm) to 633 nm light. (Soltani, Peter K., Gregory Pierce, George M. Storti, and Charles Y. Wrigley, "New Medium Wave Infrared Stimulable Phosphor for Image Intensifier Applications," [ed.] Illes P. Csorba, *Proc. SPIE* vol. 1243, 1990.) Unlike the eye-safe wavelength phosphors, these require cryogenic hardware for the phosphor upconversion plane.

RECEIVER CHOICE: As can now be seen, a great variety of technology is available for receiving eye-safe radiation and causing phosphor-responsive tube devices to respond. No demonstration, however, of pragmatically efficient operation in a lidar streak tube has been reported. Equipment adaptations accordingly have not been developed.

The foregoing discussions have noted the availability and use of very inefficient S1 detector material at 1.5 microns, and Hamamatsu's views as to its own low-efficiency detector material at that wavelength—both these materials being inadequate for industrial-quality instrumentation in the present state of the art—and also the Abbe experiments with TE material at 1.3 microns, and the suggestion by Ping of using ETIR material in streak cameras. In the absence of dispositive testing, none of these appears to represent an enabling disclosure of a commercially feasible eye-safe STIL system.

(i) Now-unrelated technologies: modern optical deflectors—Another area of technological advances that are known but have not heretofore been connected with streak lidar is microelectromechanical systems (MEMS). These devices are very small, and enable use of a simplified optical path (FIG. 11[b]).

A prominent example is a Texas Instruments product denominated a "Digital Micromirror Device" (DMD™). TI makes its DMD units for the commercial projection display market; accordingly they are readily available.

Key factors for efficient use of a DMD component include the mirror fill factor, scanning speed, uniformity of mirror motions, and quantification of diffraction effects. The DMD product has a fill factor higher than ninety percent, and can scan forty degrees in two microseconds (see Larry J. Hornbeck, "Digital Light Processing for high-brightness high-resolution applications", *A presentation for Electronic Imaging, EI '97, Projection Displays*, February 1997).

They are compatible with operation at virtually any wavelength of interest for imaging and detection—including, in particular, the eye-safe technology discussed in the preceding subsection. Again, although well established these devices have not been associated with lidar instrumentation heretofore.

As can now be seen, the related art remains subject to significant problems, and the efforts outlined above—although praiseworthy—have left room for considerable refinement.

SUMMARY OF THE DISCLOSURE

The present invention introduces such refinement. It has several main aspects or facets that are in general capable of use independently; however, using two or more of these primary aspects in combination with one another provides particularly important benefits as will be seen.

In preferred embodiments of its first major independent facet or aspect, the invention is a streak lidar imaging system. It is for measurements of a medium with any objects therein.

For purposes of the present document, this phrase "measurements of a medium with any objects therein" is hereby defined to mean that the system is for measurements of either a medium, whether or not it has any objects in it; or of objects, if any may happen to be in the medium—or of both the medium and any objects that may be in it. Thus it is not intended to suggest that necessarily objects are in the medium, or that measurements of objects will necessarily be performed if objects are in fact present, or that measurements of the medium will necessarily be performed when what is of interest is objects within the medium.

The system includes a light source for emitting at least one beam into the medium. In certain of the appended claims, this will be expressed by the language "into such medium". In the accompanying apparatus claims, generally the term "such" is used (instead of "said" or "the") in the bodies of the claims, when reciting elements of the claimed invention—for referring back to features which are introduced in preamble as part of the context or environment of the claimed invention. The purpose of this convention is to aid in more distinctly and emphatically pointing out which features are elements of the claimed invention, and which are parts of its context—and thereby to more particularly claim the invention.

The system also includes an imaging device for receiving light reflected from the medium and forming plural images, arrayed along a streak direction, of the reflected light. The imaging device includes plural slits for selecting particular bands of the plural images respectively. In addition the system includes a device for displacing all the plural images along the streak direction.

For purposes of this document, the terms "image" and "imaging" refer to any formation of an image, whether an optical or electronic image—or an image in some other domain—and also whether an image of spatial relationships as such or for instance an image of a spectrum or other spatially distributed parameter. Merely by way of example, for present purposes "image" and "imaging" may refer to images of optical-wavefront direction, or of fluorescence delay, or of polarization angle, as e.g. distributed over a beam cross-section.

The word "streak", in the present document, means substantially continuous spatial displacement of a beam—particularly in such a way that its points of impingement on a receiving screen or the like are shifted. This displacement most typically occurs during an established measurement interval, and ordinarily has the purpose of creating a substantially continuous relationship between position on such a screen and time during that measurement interval. (In classical lidar environments, but not all forms of the present invention under discussion here, a further substantially continuous relationship is thereby established between the screen position and "range"—i.e. the distance of some reflective element from the measuring apparatus.) The word "substantially" is used here so that the appended claims encompass systems and methods in which the displacement, rather than being continuous, is stepwise but only to an inconsequential degree—for instance, merely perfunctory stepping whose primary purpose may in fact be an attempt to escape the scope of the claims.

The foregoing may represent a description or definition of the first aspect or facet of the invention in its broadest or most general form. Even as couched in these broad terms, however, it can be seen that this facet of the invention importantly advances the art.

In particular, the plural slits and images enable a single streak tube to sense and record in, effectively, a space of three independent parameters rather than only two—thus curing a pervasive limitation of streak devices as mentioned earlier. The added dimension, or parameter, is extrinsic to the conventional native space of range (or time) vs. azimuth for a streak device (or indeed certain other time-resolving devices), and accordingly in this document will be called the "extrinsic dimension."

The extrinsic dimension of a streak (or other time-resolving) device is not to be confused either with the intrinsic azimuth dimension—which can be mapped by optical fibers or otherwise to represent various spatial or other parameters—or with the intrinsic range/time dimension. Rather, the extrinsic dimension is a truly independent and thus novel parametric enhancement.

Although the first major aspect of the invention thus significantly advances the art, nevertheless to optimize enjoyment of its benefits preferably the invention is practiced in conjunction with certain additional features or characteristics. In particular, preferably the imaging device includes an optical device, the plural images are optical images, and the displacing device includes a module for displacing the plural optical images.

Closely related to this preference are several subsidiary ones: preferably the displacing device includes an electromechanical device, and this in turn preferably includes at least one scanning microelectromechanical mirror—still more preferably an array of such mirrors. Alternatively it is preferable that the displacing device include an electrooptical device.

In one alternative to the optical-device preference, preferably the imaging device includes an electronic device, the plural images are electronic images, and the displacing device includes a module for displacing the plural electronic images. When this preference is observed, it is further preferable that the displacing device include electronic deflection plates. Two related electronic-implementation preferences, usually alternative to each other, are that the imaging device include (1) an optical front end that forms a single optical image of the reflected light, and an electronic stage receiving the single optical image and forming therefrom the plural electronic images; or (2) an optical front end that forms plural optical images of the reflected light, and an electronic stage receiving the plural optical images and forming therefrom the plural electronic images.

Another preference, as to the basic first main aspect of the invention, is that the displacing device form from each of the plural images a respective streak image—so that the displacing device forms, from the plural images considered in the aggregate, a corresponding array of plural streak images. In this case preferably the system further includes a device for receiving the array of plural streak images and in response forming a corresponding composite signal.

In still another basic pair of alternative preferences, the plural slits operate on the images in either optical or electronic form. Yet a further preferred way of configuring the system is to include in the imaging device a module for forming substantially a continuum of images of the reflected beam; and arrange each of the plural slits to select a particular image band from the continuum.

There are several other basic preferences related to the above-introduced first main facet of the invention. In one of these, the light source includes an optical module for emitting at least one thin, fan-shaped beam into such medium, and the imaging device includes an optical module for receiving at least one thin, fan-shaped beam reflected from such medium; at least one of these optical modules includes an optical unit for orienting a thin dimension of the reflected beam along the streak direction.

For purposes of the present document, the phrase "thin, fan-shaped beam" means a beam which—as evaluated at impingement on or exit from a medium, or at some point within the medium—is thin in one cross-sectional dimension but is fanned out in another (generally orthogonal) cross-sectional dimension. In other words, with a thin, fan-shaped beam it is possible to find some point along the beam propagation path where the aspect ratio of the beam, perpendicular to the propagation path, is much broader in one direction than in the other.

Very generally speaking a "thin, fan-shaped beam" has, at some point along the propagation path, an aspect ratio of perhaps 10:1 to 500:1 and even much higher. In special applications of the invention, however, as will be clear to people skilled in this field, the ratio may be only 5:1 or even 3:1 and remain within the reasonable scope of the appended claims. The cross-section may be rectangular, elliptical, oval or irregular, provided only that the aspect ratio is at least 3:1 or 5:1 as indicated above.

This is not a requirement that the beam have such a cross-sectional relationship at the point of transmission from the apparatus or the point of receipt into the apparatus—since in fact very commonly the beam at these particular points has a very low aspect ratio and indeed may be nearly circular. The term "aspect ratio", in turn, is used in this document in a very general sense that is common in the optics field, namely the ratio of widest to thinnest dimensions of an optical-beam cross-section (without regard to the orientations of such dimensions relative to the horizon or any other reference frame).

The point is that the aspect ratio of a thin, fan-shaped beam for purposes of this field varies greatly from the point of emission (or receipt) along the optical path—for example, rising as a transmitted beam traverses a relatively clear medium and then, within a turbid medium, changing in complicated ways as the beam continues to expand in the broader dimension but also becomes more diffuse in the thinner dimension. Therefore the aspect ratio, for purposes of this definition of a "thin, fan-shaped beam", is to be evaluated at some point where it assumes a value reasonably close to its maximum value. Thus the concept that is intended by the phrasing "thin, fan-shaped" is a mental picture of a classical old-fashioned handheld fan used to cool a person's face, and does not encompass an optical beam that merely is thin at the outset and expands to a circular or slightly oval shape.

In three other basic preferences, the imaging device includes an optical module for forming the plural images as images of the at least one reflected beam at—respectively—discrete optical wavelengths, or different polarization states, or different angular sectors, of the at least one beam. In this last case the imaging device preferably further includes an optical device for rearranging image elements in each angular sector to form a single line image for that sector; and this device in turn preferably includes remapping optics—which still more preferably include a fiber-optic or laminar-optic module, ideally a lenslet array.

Another basic preference is that the light source include an emitter for emitting light in a wavelength region at or near 1½ microns. In this case preferably the imaging device includes an upconverter for generating light at or near the visible wavelength region in response to the light at or near 1½ microns; and this upconverter in turn preferably includes phosphorescent or fluorescent material—ideally ETIR material.

Another group of basic preferences relates to the character of the medium into which the light source emit. In particular the source preferably includes some means for emitting the at least one beam into a generally clear fluid above a generally hard surface; or into a turbid medium, including but not limited to ocean water, wastewater, fog, clouds, smoke or other particulate suspensions; or into a diffuse medium, including but not limited to foliage at least partially obscuring a landscape.

In addition, as noted earlier it is further preferred that the first primary aspect or facet of the invention also be employed in conjunction with other main aspects introduced below. Many of the preferences just discussed are analogously applicable to the following main facets of the invention.

In preferred embodiments of its second major independent facet or aspect, the invention is a lidar imaging system for optical measurements of a medium with any objects therein; the system includes a light source for emitting at least one light pulse into the medium. It also includes some means for receiving the at least one light pulse reflected from the medium and for forming from each reflected pulse a set of plural substantially simultaneous output images, each image representing reflected energy in two dimensions.

For purposes of generality and breadth in discussing the invention, these last-mentioned means will be called simply the "receiving and forming means"—or sometimes just "receiving means". The "substantially simultaneous" imaging character of the receiving and forming means does not imply that the images are formed instantaneously, but rather only that formation of substantially all images in a particular set occurs during a common time interval, namely the interval during which the reflected pulse is received.

The foregoing may represent a description or definition of the second aspect or facet of the invention in its broadest or most general form. Even as couched in these broad terms, however, it can be seen that this facet of the invention importantly advances the art.

In particular, as outlined above, this aspect of the invention as broadly conceived is directed to pulsed systems, without regard to whether pulses are time resolved by streaking subsystems or by other means; such other means may encompass for instance extremely fast electronics; or instead optical circuits, processors and memories that are nowadays being devised to replace electronics. This second facet of the invention thus provides, in pulsed systems generally, a triple-parameter capability that enables range resolution (or equivalently time resolution) of two independent characteristics modulating the optical pulses—not just one such characteristic as in the past.

The term "range" as used in this document, if not otherwise specified or clear from the context, ordinarily means distance from the apparatus. As suggested earlier, this understanding is implicit in the acronym "lidar".

Although the second major aspect of the invention thus significantly advances the art, nevertheless to optimize enjoyment of its benefits preferably the invention is practiced in conjunction with certain additional features or characteristics. In particular, preferably the light source includes means for emitting not just one but a series of light pulses into the medium, each of the pulses in the series generating a corresponding such image set (in this way the receiving means generate a sequence of plural corresponding image sets); and further includes some means for storing the sequence of corresponding image sets.

Another basic preference is that the receiving means include some means for allocating image elements, in each image of the set, as among (1) azimuth, (2) range or time, and (3) an extrinsic measurement dimension. As noted earlier, the azimuth dimension may be mapped to another physical quantity as desired. In this case it is further preferred that the extrinsic measurement dimension be, selectively, wavelength, or polarization state, or a spatial selection. (The latter typically is a different spatial choice than any that is represented by azimuth, in the invention as actually used.)

Two additional basic preferences are that the receiving means include some means for causing the images in the set to be substantially contiguous; and that the receiving means include some means for receiving the reflected light pulse as a beam with a cross-section that has an aspect ratio on the order of 1:1. In this latter case it is further preferable that the light source include some means for emitting the at least one light pulse as a beam with a cross-section that, analogously, has an aspect ratio on the order of 1:1.

Yet another basic preference is that the receiving means include some means for forming the images in such a way that the two dimensions are range/time and output-image azimuth, for a particular extrinsic dimension that corresponds to each output image respectively. (In other words, when a user looks—whether visually or using viewing apparatus—at any one of the output images, what the viewer sees is an intensity plot in time or range vs. output azimuth.)

As noted earlier, this second main facet of the invention is preferably used in conjunction with certain of the other major aspects and their preferences. Thus for instance here preferably the light source includes some means for emitting the at least one beam into each of certain specific kinds of media, enumerated in the last above-stated preference for the first aspect of the invention.

In preferred embodiments of its third major independent facet or aspect, the invention is an optical system. It includes a first lenslet array for performing a first optical transformation on an optical beam; and a second lenslet array, in series with the first array, for receiving a transformed beam from the first array and performing a second optical transformation on the transformed beam.

The foregoing may represent a description or definition of the third aspect or facet of the invention in its broadest or most general form. Even as couched in these broad terms, however, it can be seen that this facet of the invention importantly advances the art.

In particular, whereas earlier uses of lenslet arrays have been limited to applications that analyze essentially static or low-frequency phenomena (e.g. only events having no significant frequency content above roughly 10 kHz), this third main aspect of the invention enables reconfiguration of optical beams into formats that are useful in time resolution of extremely fast phenomena (e.g. 1 GHz and above).

Furthermore this facet of the invention performs such reconfigurations with minimal loss of certain optical characteristics, such as—depending on the particular layout—optical phase, or wavefront orientation. This aspect of the invention thereby facilitates an advance in the art of time-resolving complicated optical signals, by five orders of magnitude.

Although the third major aspect of the invention thus advances the art to an extent that is all but astonishing, nevertheless to optimize enjoyment of its benefits preferably the invention is practiced in conjunction with certain additional features or characteristics. In particular, preferably one of the arrays includes image-plane defining lenslets to define image elements of the beam; and the other array includes deflecting lenslets to selectively deflect beam elements to reconfigure an image transmitted in the beam. In this case, preferably the one of the arrays that defines the image elements is the first array.

Another preference for this image-defining/deflecting case is that the system further include some means defining an image carried by the beam, and that the first array be positioned substantially at a focal plane of the image. In this case it is further preferable that the image-defining means include a lidar source emitting an excitation beam to a region of interest; and collection optics receiving a reflection of the excitation beam from the region and focusing the reflection at the focal plane. This preferable form of the invention is still further preferably implemented in such a way that the two transformations, considered together, include selectively imaging particular components of the beam onto plural slits following the second array; and also incorporating some means for streaking images from both slits for reimaging at a detector.

Yet another preference for the image-defining/deflecting case under discussion is that the first array also relay the image from the focal plane to the second array. In this case preferably the second array is substantially in a plane, and that plane is disposed substantially at the relayed image.

One other preference, as to the third main facet of the invention, will be mentioned here. The two transformations, considered together, include selectively imaging particular components of the beam onto plural slits following the second array.

In preferred embodiments of its fourth major independent facet or aspect, the invention is a streak lidar imaging system for making measurements of a medium with any objects in the medium. The system includes a light source for emitting into the medium a beam in a substantially eye-safe wavelength range.

It also includes an imaging device for receiving light reflected from such medium and forming an image of the reflected light. In addition the system includes an upconverter for generating light at or near the visible wavelength region in response to the reflected light (i.e. to the returning light that is in a substantially eye-safe wavelength range); and a device for displacing the image along a streak direction.

The foregoing may represent a description or definition of the fourth aspect or facet of the invention in its broadest or most general form. Even as couched in these broad terms, however, it can be seen that this facet of the invention importantly advances the art.

In particular, by means of this fourth aspect of the invention the fine range- or time-resolving capabilities of streak imaging lidar are made available for many kinds of measurements that otherwise would be precluded by proximity to unprotected people. In some relatively small-scale applications, such people might be simply passersby in a laboratory, or in an industrial or like environment—and in applications at a larger scale such people might be members of a general population. It has not previously been suggested that the temporal resolving power of streak lidar systems could be exploited for such applications.

Although the fourth major aspect of the invention thus significantly advances the art, nevertheless to optimize enjoyment of its benefits preferably the invention is practiced in conjunction with certain additional features or characteristics. In particular, in alternative preferences the upconverter may be positioned in the system either after or before the displacing device.

Preferably the upconverter includes phosphorescent or fluorescent material, and most preferably ETIR material. The light source preferably emits the beam in a wavelength range at substantially 1½ microns.

In preferred embodiments of its fifth major independent facet or aspect, the invention is a streak lidar imaging system. It includes a light source for emitting a beam, and an imaging device for receiving light originating from the source and for forming an image of the received light.

The system also includes at least one microelectromechanical mirror for displacing the image along a streak direction. In addition it includes an image-responsive element for receiving and responding to the displaced image.

The foregoing may represent a description or definition of the fifth aspect or facet of the invention in its broadest or most general form. Even as couched in these broad terms, however, it can be seen that this facet of the invention importantly advances the art.

In particular, this fifth main aspect of the invention enables enjoyment of streak-lidar capabilities without the inordinate expense and fragility of an evacuated streak tube with its associated high voltages and relatively temperamental drive electronics—and also without the previously discussed cumbersomeness and very limited operating properties of a macroscopic scanning mirror, such as a relatively large spinning polygon.

Although the fifth major aspect of the invention thus significantly advances the art, nevertheless to optimize enjoyment of its benefits preferably the invention is practiced in conjunction with certain additional features or characteristics. In particular, preferably the at least one mirror includes an array of multiple microelectromechanical mirrors.

In case the system is for use with an optical medium, another preference is that the light source include some means for emitting the beam into the medium—and that the imaging device include some means for receiving light reflected from the medium and forming an image of the reflected light.

Another basic preference, as to this fifth main facet of the invention, is that the light source include a resonant device and the imaging device include some means for causing imperfections in resonance of the resonant device to modulate the image. In this case, particularly if the resonant device includes a laser, it is also preferred that the imaging device include some means for causing imperfections in optical wavefronts from the laser to modulate the image—and further preferably these causing means include some means for deflecting elements of the beam in response to local imperfections in the coherence. These deflecting means, in turn, preferably include at least one lenslet array.

In preferred embodiments of its sixth major independent facet or aspect, the invention is a spatial mapping system for mapping a region. The system includes a light source for emitting at least one thin, fan-shaped beam from a moving emission location toward the region; a thin dimension of the beam is oriented generally parallel to a direction of motion of the emission location.

The system also includes an imaging device for receiving light reflected from such region and forming an image of the reflected light. The system also includes some means for separating the reflected light to form plural reflected beam images—representing different aspects of the region, respectively.

Here the term "aspects" means characteristics or properties of the region. It is to be interpreted broadly to include different values of any parameter that is susceptible to probing by an optical spatial-mapping system. Merely by way of example, such a parameter may be spatial, dynamic, optical, chemical, acoustic, biological or even sociological.

Also included is an image-responsive element for receiving and responding to the plural beam images. The foregoing may represent a description or definition of the sixth aspect or facet of the invention in its broadest or most general form.

Even as couched in these broad terms, however, it can be seen that this facet of the invention importantly advances the art. In particular, a thin fan beam or plural such beams can be used to yield a representation of two or more values of any optical parameters—expanding the usefulness of a pushbroom mapping system into a three-dimensional regime, with the selected parameter functioning as the third dimension.

Thus with this aspect of the invention it is not necessary to be limited to mapping spatially at just one wavelength, or in just one polarization state—or even at only one visual angle, one pair of subtended angular widths, or one focal condition. Subject to laser-technology limitations, a single emitter may be made capable of emissions at more than one coherence length; and this would enable application of the invention with coherence length as the extrinsic parameter.

Although the sixth major aspect of the invention thus significantly advances the art, nevertheless to optimize enjoyment of its benefits preferably the invention is practiced in conjunction with certain additional features or characteristics. In particular, there are several preferences regarding capability of the separating means to discriminate between different aspects of the probed region: spatially different aspects, or aspects that are carried in portions of the beam received at different angles, or in portions of the beam received at different angular ranges, or in different polarization states of the beam, or in different spectral components.

Another basic preference is that the separating means include means for discriminating between combinations of two or more different aspects of the region that are carried in different characteristics of the beam, at least one of which characteristics is selected from among spatially different aspects, different polarization states, and different spectral components of the beam. In this case preferably at least two of the characteristics are selected from among those three enumerated characteristics.

Yet another basic preference is that the emission location be a spacecraft, an aircraft, another type of vehicle, or another type of moving platform. As an alternative, preferably the emission location is a fixed light source cooperating with a scanning system to provide a moving image of the light source. Also applicable here are the previously enumerated preferences as to type of medium into which the beam is emitted.

In preferred embodiments of its seventh major independent facet or aspect, the invention is a spatial mapping system for mapping a region. The system includes a light source for emitting a beam whose cross-section has an aspect ratio on the order of 1:1, from a moving emission location toward the region.

It also includes an imaging device for receiving light reflected from such region and forming an image of the reflected light; and some means for separating the reflected light to form plural reflected beam images representing different aspects of the region, respectively. Also included is an image-responsive element for receiving and responding to the plural beam images.

The foregoing may represent a description or definition of the seventh aspect or facet of the invention in its broadest or most general form. Even as couched in these broad terms, however, it can be seen that this facet of the invention importantly advances the art.

In particular, this form of the invention extends broad-beam imaging to three-parameter measurement space, analogously to the extension introduced above for thin fan-beam work. As will be seen, the benefits of this extension are felt in ability to obtain much more sophisticated image interpretations, in a variety of applications.

Although the seventh major aspect of the invention thus significantly advances the art, nevertheless to optimize enjoyment of its benefits preferably the invention is practiced in conjunction with certain additional features or characteristics. In particular, preferably the imaging device includes some means for also receiving the reflected light from the region as a reflected-beam whose cross-section has an aspect ratio on the order of 1:1.

In preferred embodiments of its eighth major independent facet or aspect, the invention is a spectrometric analytical system for analyzing a medium with any objects therein. The system includes a light source for emitting substantially at least one pencil beam toward the medium, and an imaging device for receiving light reflected from such medium and forming an image of the reflected light.

Also included are some means for separating the reflected light along one dimension to form plural reflected beam images arrayed along that "one dimension" and representing different aspects of the medium, respectively. The system further includes optical-dispersing means for forming a spectrum from at least one of the plural images, by dispersion of the at least one image along a dimension generally orthogonal to the one dimension—and an image-responsive element for receiving and responding to the plural beam images.

The foregoing may represent a description or definition of the eighth facet of the invention in its broadest or most general form. Even as couched in these broad terms, however, it can be seen that this facet of the invention importantly advances the art.

In particular, this eighth main facet of the invention provides the benefits of an added extrinsic parameter, in the context of hyperspectral measurements. In particular through use of this eighth facet of the invention it is possible to obtain spectra for different aspects of the medium or objects—as for different values of the optical properties listed above in discussion of the first preferences for the sixth facet of the invention.

Although the eighth major aspect of the invention thus significantly advances the art, nevertheless to optimize enjoyment of its benefits preferably the invention is practiced in conjunction with certain additional features or characteristics. In particular, preferably the dispersing means include means for forming a spectrum from each of the plural images, respectively.

Other preferences are that the separating means include some means for separating the reflected light to form plural images representing aspects of the beam that, respectively, are spatially different—or represent different polarization states or different spectral constituents.

In preferred embodiments of its ninth major independent facet or aspect, the invention is a wavefront sensor, for evaluating a light beam from an optical source. The sensor includes optical components for receiving the beam from the source.

It also includes optical components for subdividing small portions of such beam to form indicator subbeams that reveal a direction of substantially each of the small portions; and optical components for steering the indicator subbeams to fall along at least one slit. The sensor also includes some means for streaking light that passes through the at least one slit; and some means for capturing the streaked light during a streaking duration.

The foregoing may represent a description or definition of the ninth aspect or facet of the invention in its broadest or most general form. Even as couched in these broad terms, however, it can be seen that this facet of the invention importantly advances the art.

In particular by steering the subbeams to fall along a slit, the sensor provides an output that enables the aggregate of those subbeams to be streaked—and thereby makes it possible to time resolve the directional or other behavior of the subbeams. Because many subbeam sets can be arrayed along even just a single slit, wavefront directions can be time resolved for many points in the beam cross-section.

Although the ninth major aspect of the invention thus significantly advances the art, nevertheless to optimize enjoyment of its benefits preferably the invention is practiced in conjunction with certain additional features or characteristics. In particular, preferably the at least one slit comprises plural slits. (This preference raises very greatly the number of points in a beam cross-section that can be time resolved.)

In another preference, particularly for use with a resonant optical source, the receiving and subdividing components include means for causing imperfections in optical wavefronts from the resonant source to modify the light that passes through the at least one slit. In this case preferably the receiving, subdividing and steering components include at least one lenslet array—and more preferably at least two lenslet arrays in optical series.

In this latter arrangement preferably the lenslet arrays include one array that defines image elements at or near a focal plane of the beam, and another array that receives the image elements relayed from the first array, and that steers light from the image elements to the at least one slit. An alternative basic preference is that the receiving, subdividing and steering components comprise at least one lenslet array in optical series with at least one fiber-optic remapping device—in other words, that the steering function be performed by fiber-optic remapping rather than the other array just mentioned.

In preferred embodiments of its tenth major independent facet or aspect, the invention is a spectrometric analytical system for analyzing a medium with any objects therein. The system includes a light source for emitting substantially at least one pencil beam toward the medium, and an imaging device for receiving light reflected from such medium and forming an image of the reflected light.

It also includes optical or electronic means for streaking the plural images, and an image-responsive element for receiving and responding to the plural beam images. Also included is a computer for extracting fluorescence-lifetime information from a signal produced by the image-responsive element.

The foregoing may represent a description or definition of the tenth aspect or facet of the invention in its broadest or most general form. Even as couched in these broad terms, however, it can be seen that this facet of the invention importantly advances the art.

In particular, this hybrid form of the invention uniquely combines capabilities of earlier-discussed facets. It does so in such a way as to provide from a single apparatus information about biological materials in volume materials—such as clouds—that heretofore would strain the capabilities of two or more different instruments.

Although the tenth major aspect of the invention thus significantly advances the art, nevertheless to optimize enjoyment of its benefits preferably the invention is practiced in conjunction with certain additional features or characteristics. In particular, preferably the at least one beam includes at least one pencil beam.

Also preferably the imaging device includes a hyperspectral optical system. In this case it is further preferred that the imaging device include a plural-wavelength optical system, in which each of plural wavelength bands is arrayed along a length dimension of a respective slit-shaped image.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is an elevation, highly schematic, of conventional streak-tube architecture;

FIG. 2 is a pair of simplified diagrams showing (a) in perspective or isometric view, typical STIL data collection in a plane that extends away from the instrument through and beyond an object of interest; and (b) an elevation of a resulting CCD image for the same measurement setup;

FIG. 7 is an elevational diagram, somewhat schematic, of streak-tube receiver architecture for plural-slit (in this case as in FIG. 6, three-slit) operation;

FIG. 8 is a set of four diagrams—three plan views and one isometric—showing how a simple area image can be remapped onto plural lines suitable for input into the plural-slit streak tube: (a) the original area image, (b) the area image rearranged into plural lines (here four) by remapping optics, (c) the relationship between the first two views, and (d) a deformed, sliced, and reassembled fiber-optic device performing the transformation shown in the first three views;

FIG. 11 is a set of two elevational diagrams, both highly schematic, and an artist's perspective or isometric rendering showing respectively (a) conventional optical streaking by means of a large rapidly rotating mirror, (b) innovative optical streaking with MEMs mirrors and no other moving parts, and (c) a more-specific novel design with DMDs;

FIG. 12 is a diagram like FIG. 7, but showing a further modification for plural-slit spectroscopy—with a wavelength dispersion device arranged to array the available spectrum along the height of the photocathode plane, and at the photocathode a preferably programmable slit-mask device (e.g. spatial light modulator) for selecting particular plural spectrally narrow wavebands specified for a desired spectral analysis; as well as streaked forms of those wavebands appearing on the anode at right;

FIG. 13 is a set of three diagrams showing, for the FIG. 12 system, respective phenomena related to the image as it progresses through the front-end components: (a) the vertically dispersed spectrum at the entrance to the slit-mask device, (b) the programmable mask itself, here set for three slits at specified heights, and (c) the resulting selected image on the photocathode—consisting of three isolated line images in respective shallow wavebands;

FIG. 18 is an isometric diagram of fore-and-aft viewing using two fan beams to simultaneously acquire plural (here only two) different views of every object;

FIG. 19 is a set of three diagrams illustrating image-distorting effects of water waves: (a) ray deviations, for rays to and from certain submerged objects, shown for a given surface, (b) images and associated SNRs of the same objects but showing various distorting effects for rays incident normally, and (c) images of the same objects for rays coming in at 30 degrees off normal—showing different object shapes, locations and SNRs;

FIG. 21 is a set of three diagrams representing an example of measuring a covered hard object with a polarization-sensitive two-slit STIL: (a) a vertically projected fan beam intersecting the object on the ground, (b) streak camera images from a single laser shot showing at left the respective images in two generally orthogonal polarization states—and at right the corresponding cross-sectional views—and (c) reconstructed images from multiple shots;

FIG. 24 is a pair of illustrations relating to data from a preferred embodiment of a hyperspectral form of the invention: (a) a graphic showing how the spectral dimension is arrayed along the length of the slit—rather than across the width dimension—and (b) to essentially the same spectral scale, a reproduction of actual excitation and fluorescence image data acquired in a representative measurement;

DETAILED DESCRIPTION OF THE PREFERRED EMBODIMENTS

1. Plural-Slit System for Single-Pulse Scanless 3-D Imaging

Conventional underlying streak-tube concepts have been introduced above—in subsection 2 of the earlier "BACKGROUND" section. In those conventional approaches, a system transmits and receives a single narrow fan beam.

The present invention proceeds to a new technique, plural-slit streak-tube imaging lidar (PS-STIL)—with associated plural line images, and other resulting plural parameters. This innovation provides a much more general solution to a number of lidar applications than possible with a single line image per laser shot.

As usual, "plural" means "two or more". This term thus encompasses "multiple"—i.e. three, four etc.—slits as well as associated multiple images, multiple wavelengths and other corresponding parameters.

Figure 3A:
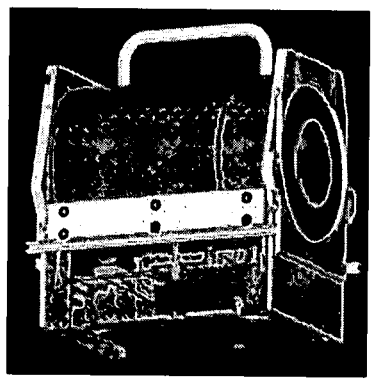
FIG. 3 is a pair of perspective views showing (a) a ruggedized streak-tube assembly and (b) a three-dimensional model of a two-receiver lidar system fabricated to fit into a very small volume, e.g. of an unmanned underwater vehicle.
Figure 3B:
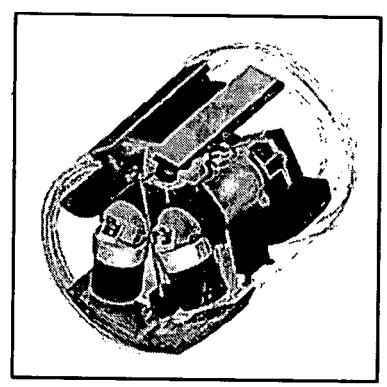
Figure 4A:
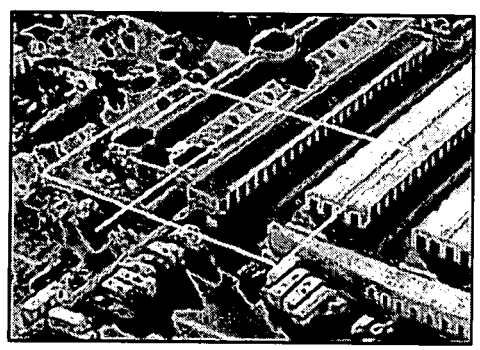
FIG. 4 is a set of illustrations relating to conventional-STIL terrestrial mapping data, including (a) an aerial photo of buildings being surveyed, (b) a single laser shot showing raw data for one line image (outlined by a rectangular white line in [a]), and (c) a three-dimensional rendered range image of a corresponding area (outlined in [a]) generated by reconstruction from the individual line images (brighter is taller)
Figure 4B:
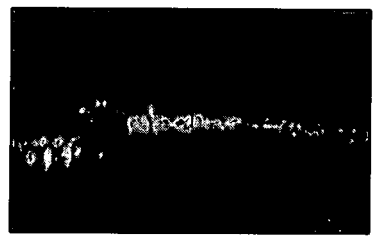
Figure 4C:
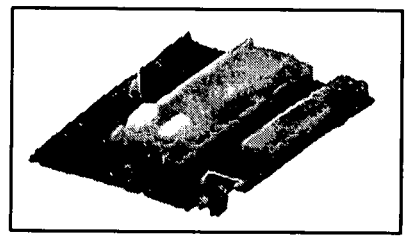
Figure 5A:
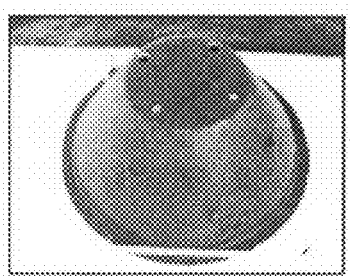
FIG. 5 is a set of five images relating to data acquired by conventional STIL imaging of an object submerged in shallow water, including (a) a photo of the bottom object used in the experiment, (b) a contrast/reflectivity image of the object at a depth of 6 m (20 feet), (c) a range image of the same object, in which brighter rendering represents greater proximity to the instrument, (d) a three-dimensionally-rendered surface, with contrast data mapped onto the surface, and (e) a one-dimensional cut through the range image, with actual object profile, showing an excellent match between data and object.
Figure 5B:
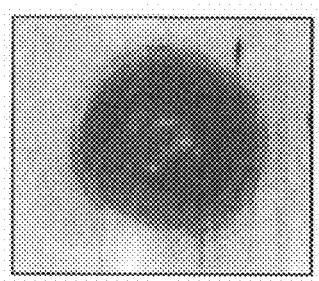
Figure 5C:
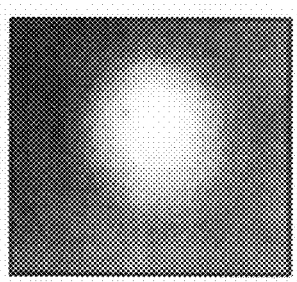
Figure 5D:
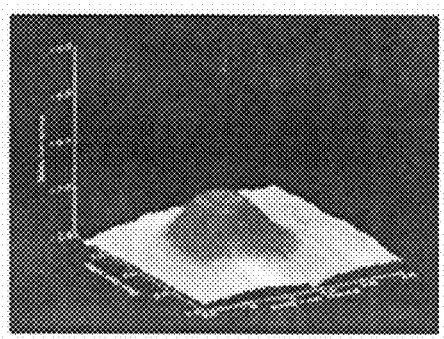
Figure 5E:
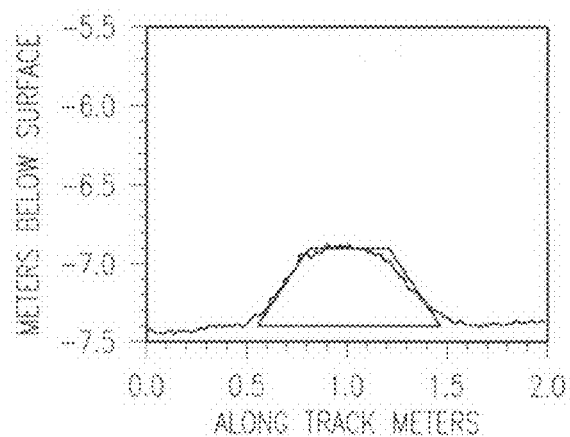
Figure 6A:
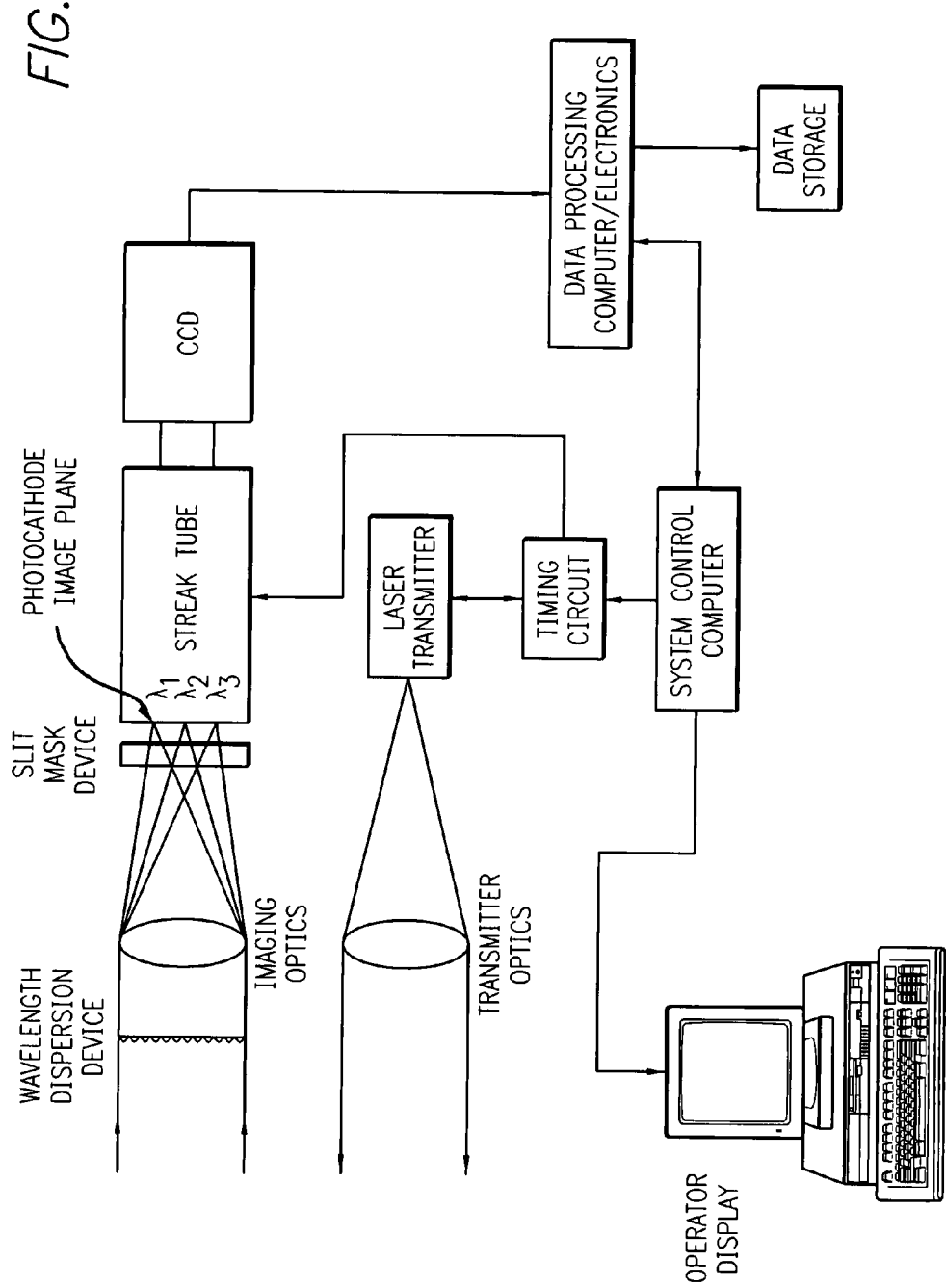
FIG. 6 is a set of three diagrams showing general characteristics applicable to several different forms of the invention: (a) system block diagram, (b) wavelength dispersion methods, and (c) data-processing algorithms and hardware implementations.
Figure 6B:
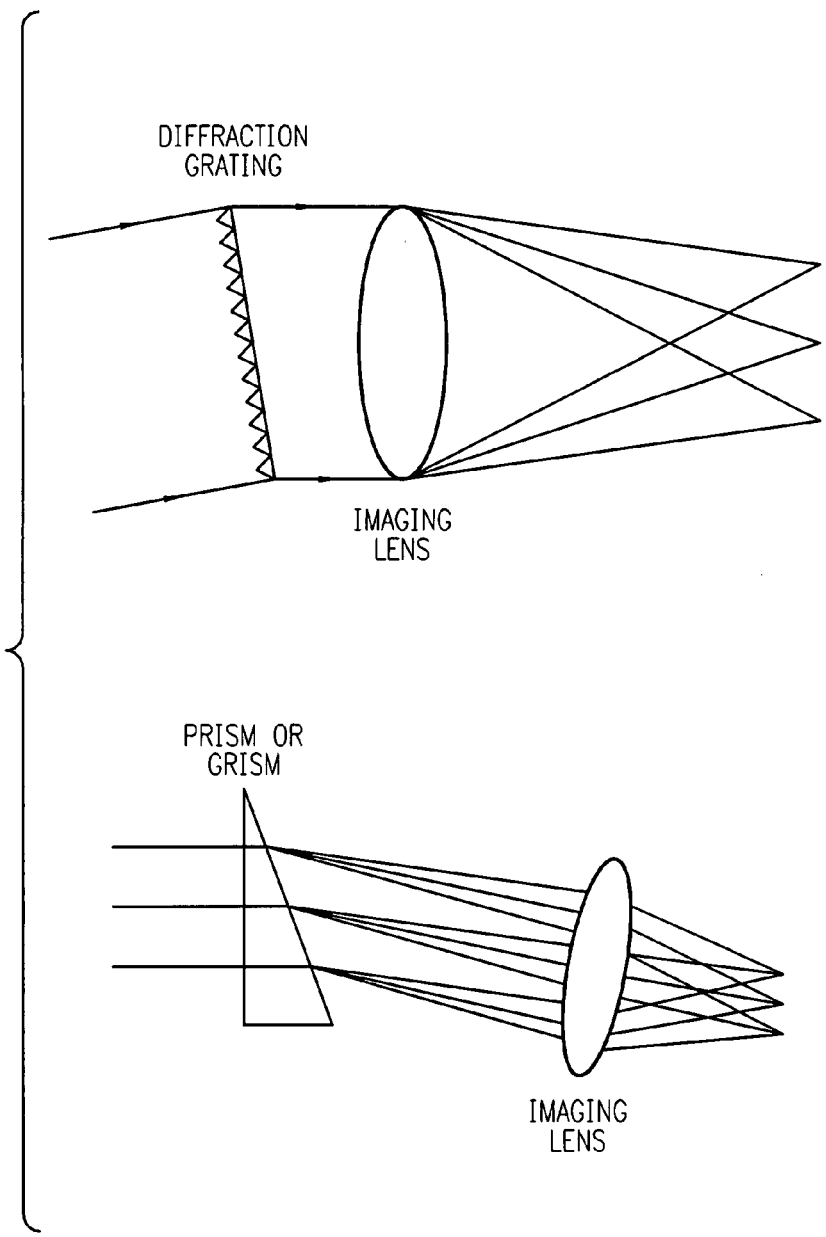
Figure 6C:
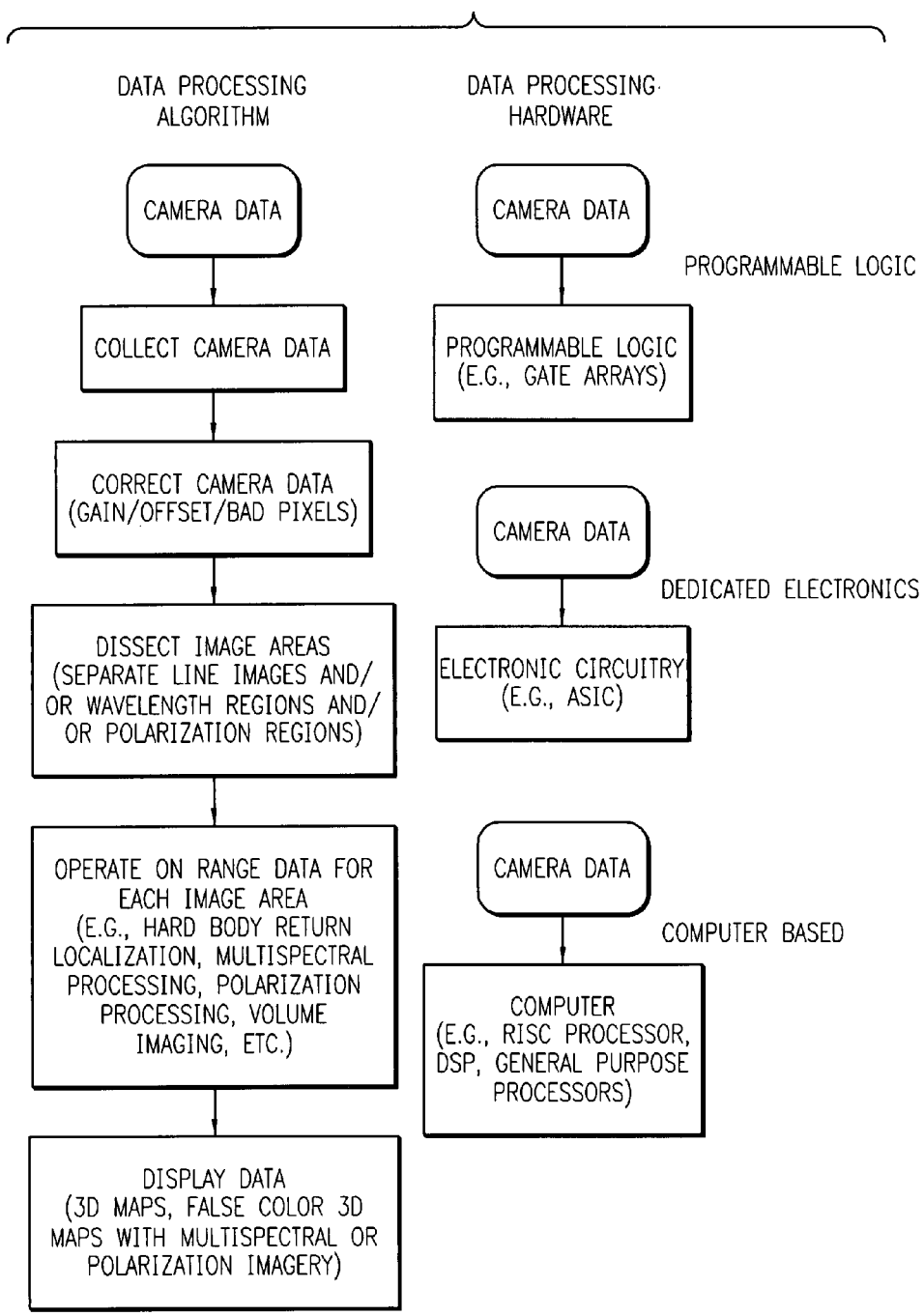

Basically, the PS-STIL approach to streak-tube imaging provides plural, contiguous range-azimuth images (FIGS. 6[*a*] and 6[*b*]) per laser pulse. Each shot thereby yields a full three-dimensional image.

All three of these dimensions can be, but are not necessarily, spatial dimensions. The third dimension—the one other than range (or time) and azimuth—may instead be virtually any parameter that has an optical manifestation.

Such a parameter may be for instance focal length, or wavelength, or coherence length, or polarization angle, or the subtended angle or other property of a beam or subbeam. (It is not intended to suggest that these particular examples are particularly preferred embodiments of the extrinsic dimension or even that they are particularly useful choices—but rather only that the available range of choices for that dimension may be extremely broad.)

The plural-slit STIL technique of the present invention, however, does enable collection of two-spatial-dimension area images rather than line images. It also thereby enables formation of true single-pulse three-spatial-dimensional images.

Each slit forms its own image zone on the phosphor anode (or other receiving surface such as will be considered below). The plural-slit system requires no modification to the streak tube or CCD (although such modification can be provided for further enhancement if desired); the system can be implemented through use of external front-end remapping optics that convert an image into plural separated line images.

The plural-slit technique takes advantage of the fact that many of the pixels ordinarily dedicated to range are unused in the conventional single-slit configuration. After careful study of such relationships, a system designer—or advanced operator—can therefore reassign pixels to provide additional spatial (or other) information instead.

By parceling out image regions into plural lines on the streak-tube photocathode, the invention can trade-off range pixels against spatial (or other) pixels. In this way the invention provides an additional degree of freedom, that can be used in any of several ways to better optimize the system for a given application.

One preferred way to implement the plural-image feature of the invention is simply to form corresponding plural optical slits—i.e. masks or baffles (FIG. 7)—on the photocathode. As the drawing suggests, this technique does not require changes to the streak tube itself (although optimizing refinements, as mentioned above, are encompassed within the scope of the invention), but can be a change in front-end optics only. Several other ways of forming and streaking plural images are introduced below (particularly in subsection 4).

Further exploiting this novel arrangement, an area image can now be remapped by fiber-optic devices (FIG. 8), by lenslet arrays, or in other ways into plural line images—not just one as in the previous fiber-optic systems of Alfano or of Knight. Such plural line images can then be directed for input into the plural-slit streak tube.

Many other ways to make use of this newly added degree of freedom are within the scope of the present invention. Several such innovations are detailed below in subsections 4 through 7. The invention is adaptable to most uses of the now-standard STIL technology, including airborne bathymetry, airborne detection of fish schools and various other utilizations mentioned in related patent documents of Areté Associates and its personnel.

2. Eye-Safe Operation, and Related Innovations

Converting STIL technology to eye-safe wavelengths entails conversion of both the transmitter and the receiver.

(a) Using electronic tube with selected detector materials—It appears to the present inventor that phosphor upconversion promises to be the simplest and most straightforward technique for moving to the eye-safe regime. It also appears to the inventor that in particular the class of phosphors called "electron-trapping infrared" (ETIR) up-conversion phosphors is the best of the candidates, based on the simplicity of its application to photocathode surfaces—although testing in STIL cameras has not been reported.

Collaboration with the Lumitek firm mentioned earlier, or an alternative source, is advisable for implementation of ETIR phosphor films. Samples of the Q-32-R phosphor film are a good starting point and have been evaluated by the inventor for sensitivity, resolution, and temporal pulse spreading. For STIL testing the ETIR film should be deposited on the fiber-optic faceplate of the streak tube, and actual lidar data taken in both the lab and the field.

Also desirable is provision of a 1.5 micron source—as e.g. by conversion of an existing Nd:YAG laser, through addition of an optical parametric oscillator (OPO). LiteCycles, a manufacturer of YAG lasers also mentioned earlier in this document, can perform such work—particularly for that firm's own products.

(b) Using optical streaking—A new variant according to the present invention is to use a MEMS Digital Micromirror Device (DMD™) product that scans the beam without the use of large moving mirrors, thus allowing the system to be compact and rugged. As will be recalled, such units are available as an off-the-shelf component from Texas Instruments, though such usage in a streak imaging lidar system has not been suggested earlier. This technique allows for longer-wavelength operation—thereby promoting the previously noted specialized applications that call for better penetration and discrimination—and also provides a substitute methodology for the eye-safe regime, for situations in which the ETIR phosphor may prove inadequate.

Figure 12A:
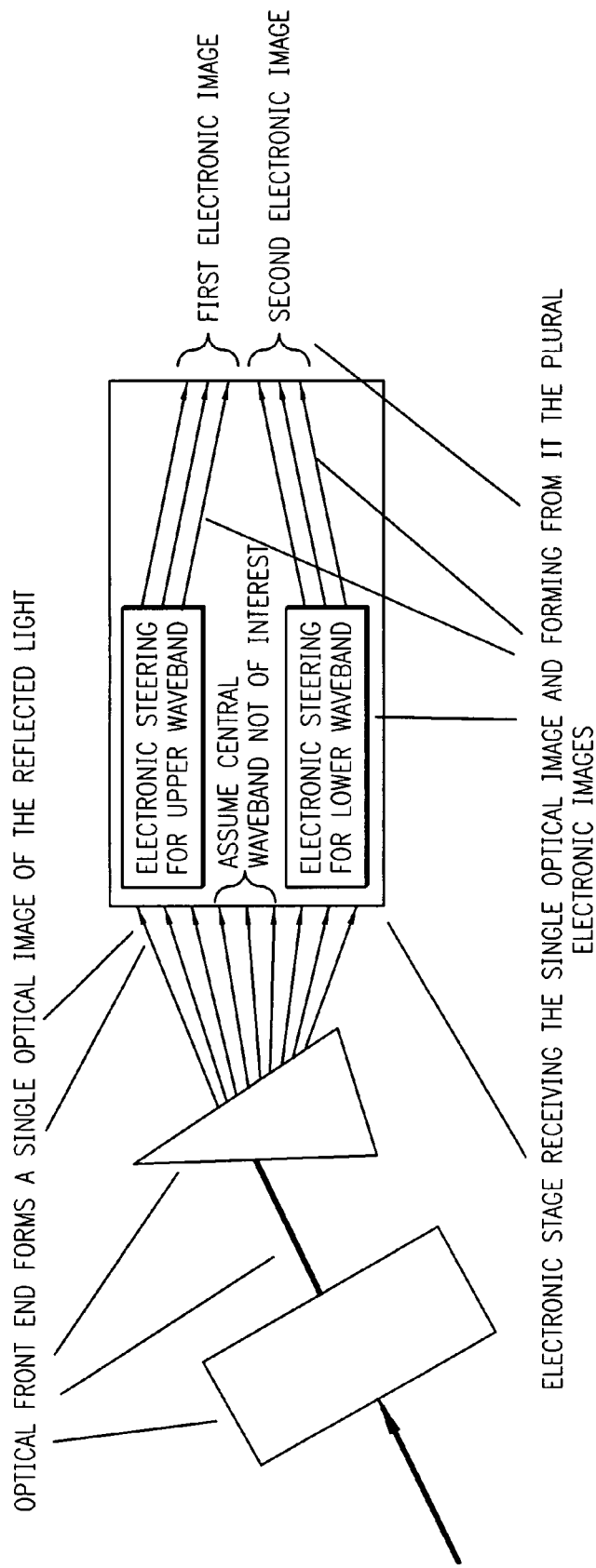
FIG. 12(a) is a like diagram but using an electronic, rather than optical, form of slit masking—with the selective plural-slit mask now inside the tube, following the photocathode.
Figure 12B:
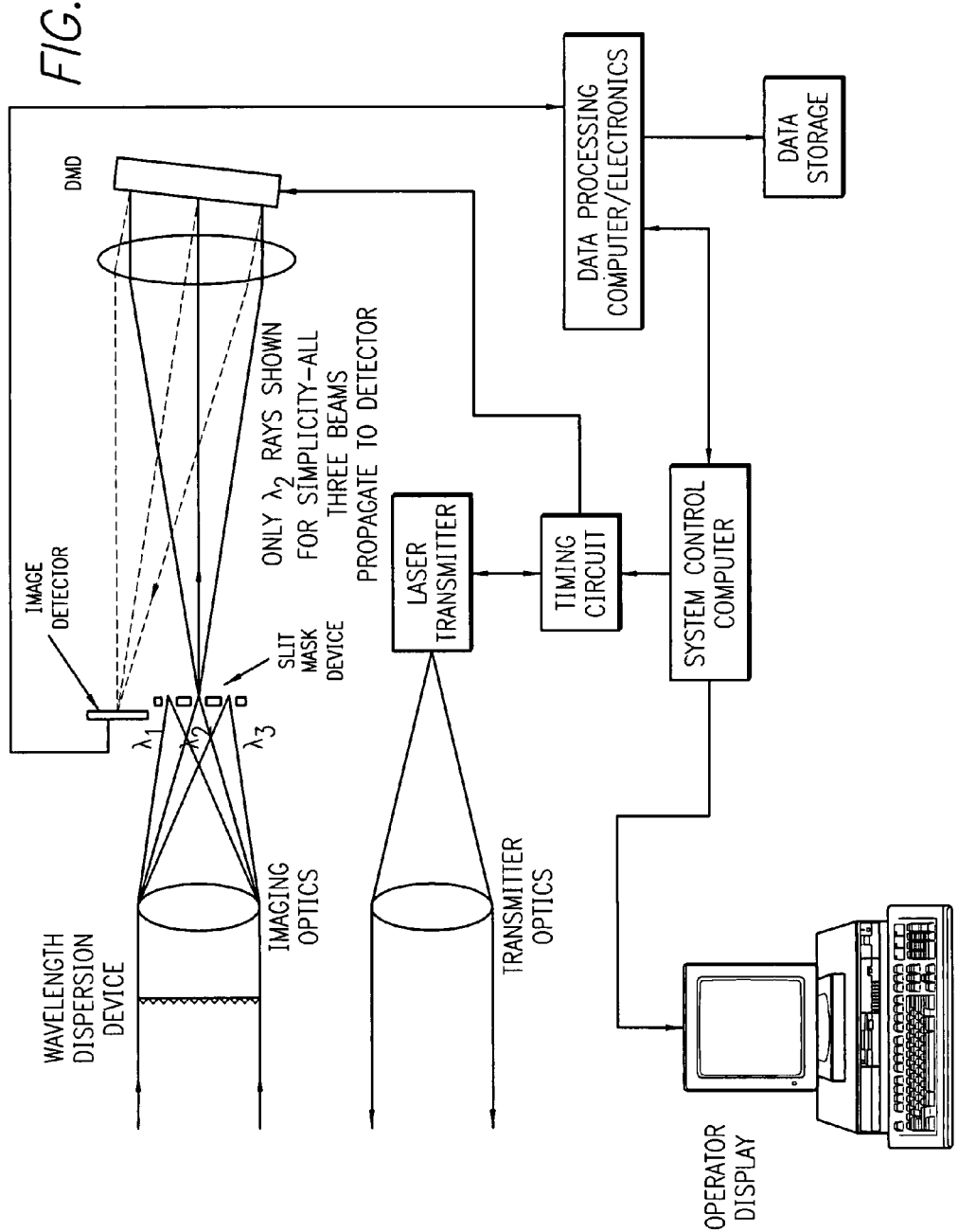
FIG. 12(b) is a diagram like FIG. 12 but showing an optical, rather than electronic, form of streaking—which obviates the need for an evacuated tube and also represents one way of facilitating use of wavelengths outside the visible range.

A MEMS-based PS-STIL sensor uses the motion of the MEMS elements to provide the optical streaking. The beams enter the MEMS sensor (FIG. 12[b]) through a series of slits, closely analogous to the arrangement when a streak tube is used, and the beams are reimaged by a lens to form a new image on the detector.

Putting a MEMS mirror (labeled "DMD" in the figure) behind the lens as shown, and bouncing the light back through the lens, has an important result: the MEMS mirror can then be used near a pupil plane, where the scanning motion of the MEMS elements is translated into motion in the image plane (at the detector). Attempting to place the MEMS element at a focal plane and then reimaging that focal plane onto the detector would result in no streaking.

The rest of the system is closely similar to the streak-tube-based systems. Software and control-electronics modifications are needed only as appropriate to accommodate the specific detailed relationships between the beam, at the detector, and given mirror-control commands.

It appears that a MEMS optically streaked camera can be very compact. In fact the invention contemplates that size limitations are determined by the IR detector array, rather than the streak-tube assembly. Thus the main details are diffraction effects and mirror-response uniformity during scanning.

Nonuniformity of motion generates a blur in the range direction, and diffraction from the small mirrors can cause blurring in both the range and spatial directions. Based on the discussion here and in the papers method, these aspects of DMD performance are straightforwardly calculated and optimum configurations then found accordingly.

Available DMD scanning speeds allow for 1 GHz range sampling on a 25 mm (1 inch) detector that is spaced 70 mm from the DMD scanner. DMD units are compatible with operation at any wavelength for which a standard area imaging sensor is available (e.g. 300 nm to 5 microns).

IR detectors and optical streaking, for present purposes, must be implemented with care to avoid disrupting the plural-slit functionality of the present invention—which is also accomplished optically.

(c) Longer-wavelength operation—A microelectromechanical DMD™ device, mentioned above, can be procured from Texas Instruments and straightforwardly integrated into a streak-camera configuration. The resulting instrument is particularly effective for special applications that exploit longer wavelengths as pointed out previously.

Uniformity of mirror motion and diffraction effects should be measured, and for relative safety and simplicity of operation most or all of this preliminary laboratory phase can be carried out with the system operating in the visible. Of course care must still be taken to avoid eye injury.

Those skilled in the field will understand that actual diffraction is of course different when the unit is put into service in the infrared; but also that the behavior in the two wavelength regions is related in simple and very predictable ways. For infrared operation it is also advisable to determine the emissivity of the DMD unit itself, in the anticipated actual operating region of 1 to 5 microns—and its utility in that region.

For this purpose, collaboration with infrared astronomers may be found particularly helpful; for example, the present inventor has made arrangements with such scientists at Steward Observatory, a facility of the University of Arizona. A 3-to-5-micron streak camera system is a good initial implementation for practical testing, familiarizing personnel with operation and use as a platform for possible redesign to satisfy specific requirements of the intended application.

3. Signal-Processing Refinements

As mentioned earlier, conventional real-time range processing typically uses multiple SHARC digital signal processors (DSPs), each capable of 120 Mflop/sec (million floating-point operations per second). Through porting of existing and proven algorithms to run on a single field-programmable gate array (FPGA), throughput can be enormously increased.

Such units are available from the previously mentioned firm Nallatech Limited, of Glasgow. Nallatech has demonstrated image processing at 100 Gflop/sec (billion floating-point operations per second).

More specifically Nallatech's demonstration entailed a matched-filter convolution of a 13×13-pixel kernel on a 1024×1024 image at 1000 Hz. This increase by three orders of magnitude was accomplished in part by configuring the FPGA hardware specifically for the image-processing task.

An FPGA-based range-processing scheme can save considerable volume and power over a real-time DSP solution. The associated reduction in computer size makes practical a short-range system that can be carried by a person—in this way resolving a previously discussed major problem of the prior art, as well as reducing weight, volume, power, and heat-loading in vehicle-mounted sensors.

In addition the very compact systems enabled by the FPGA approach can devote all possible power to the laser transmitter rather than the processing hardware. Power allocated to the transmitter directly improves system performance, thus optimally actualizing the plural-slit technique of the invention with maximum detection SNR in a single receiver.

Collaboration with Nallatech is advisable before specifying the interfaces and algorithms to be implemented. Nallatech can develop a first-effort processor using the firm's hardware known as "DIME" (DSP and Image-processing Module for Enhanced FPGAs). This is a plug-and-play PCI board, with two FPGAs that work in a standard PC. Timing and performance of the selected algorithm should be evaluated and compared with the performance of a standard algorithm run on DSPs.

4. Spectral-Resolution Forms of the Invention

The plural-image technique allows tremendous gains in ability to simultaneously and independently resolve spectral, temporal and spatial portions of a lidar signal, all within the same excitation pulse. These forms of the invention represent extension of pixel-remapping concepts into the spectral domain.

This approach can provide a simplified and more robust mode of fluorescence imaging in detecting and measuring atmospheric particulates and constituents, waterborne particulates, and hard objects (with propagation paths in either air or water). Simultaneous measurement of all pertinent signal parameters, within a common laser pulse, removes many hardware requirements and noise terms associated with use of multiple pulses to gather all of these data.

For example the laser-pulse power, pulse shape and pulse timing are all the same for an entire data frame; therefore any artifacts that would be caused by differences in these quantities are absent. In addition, absolute calibration requirements that do remain are significantly reduced.

Timing within an area is all internally consistent. The only persisting problem of this sort must arise from jitter between the start of the laser pulse and the start of the electronic receiving system.

The invention facilitates high levels of digitization and sampling—achieved by spreading out temporal data spatially on a streak-tube screen—and so enables extremely fine resolution in critical dimensions. The system can trade-off resolution between wavelength, time and space in order to optimize performance for a given application.

Digitization to twelve bits and better, with up to 1000 channels sampled simultaneously at over 100 GHz, is far beyond anything that can be done with conventional analog-to-digital conversion electronics. For instance 1000 channels of twelve-bit digitization at only 100 MHZ would require approximately a hundred VME-size boards (computer-bus type, chassis/backplane units).

As explained above, the plural-slit technique employs two or more slits, stacked in the streak direction, to provide an additional dimension to the data set. Here the additional dimension is made to correspond to wavelength. The streaking electronics require additional controls to avoid having the streaked image from one wavelength band overlap the streaked image from another.

In one form of hardware suitable for performing plural-slit spectroscopy, a wavelength dispersion device (FIG. 12) distributes the wavelength spectrum along the photocathode plane, but just ahead of the photocathode a slit-mask device (a spatial light modulator, for example) forms a programmable set of slits for selecting desired wavelength bands from the spectrum.

The spectrum image (FIG. 13) reaches the cathode, then (to the same scale) the programmable mask, and finally the image on the photocathode. The latter is a set of discrete line images at respective different wavelengths or, more precisely, narrow wavebands.

Alternative hardware applies the entire dispersed image (FIG. 12[a]) to the photocathode—producing a corresponding unitary electronic image, within the evacuated tube, representing the full spectral image. Masking or electronic selection within the tube then performs the selection process.

The streak-tube electronics subsystem then streaks these images to create a set of wavelength regions on the phosphor anode that have both time and space data at each wavelength. Thus each wavelength region has its own time- and space-resolved image.

An alternative to the electronic streaking just described is optical streaking. In accordance with the present invention this can be accomplished using microelectromechanical devices—developed commercially for quite different purposes—that make the streak lidar apparatus (FIG. 12[b]) far more compact and robust than possible with the spinning polygon mirrors historically employed.

This section introduces various applications of such a device. It also discusses in more detail the data in each of the individual wavelength regions.

A number of trade-offs between the various dimensions of resolution are available. The total number of sampled points is, at most, equal to the total number of pixels in the CCD. To first order, the product of the number $n_\lambda$ of discrete wavelength bands, the number $n_S$ of spatial points, and the number $n_T$ of time points must be equal to or less than the number $n_P$ of pixels.

For schemes that are more complicated (compared with those shown in FIGS. 12 and 13), there are a number of options involving wavelength dispersion elements and the imaging optic—to allow for nearly any desired mapping of time, space and wavelength on the streak-tube screen and CCD. Discussed below are a few simple examples showing how a plural-image device can be useful.

Although many other examples could be given, these are reasonably representative. In all these applications the streak-tube receiver is assumed to be coupled with a pulsed laser system that provides the excitation sources for phenomena to be observed (e.g. fluorescence, Raman shifts etc.).

Figure 14:
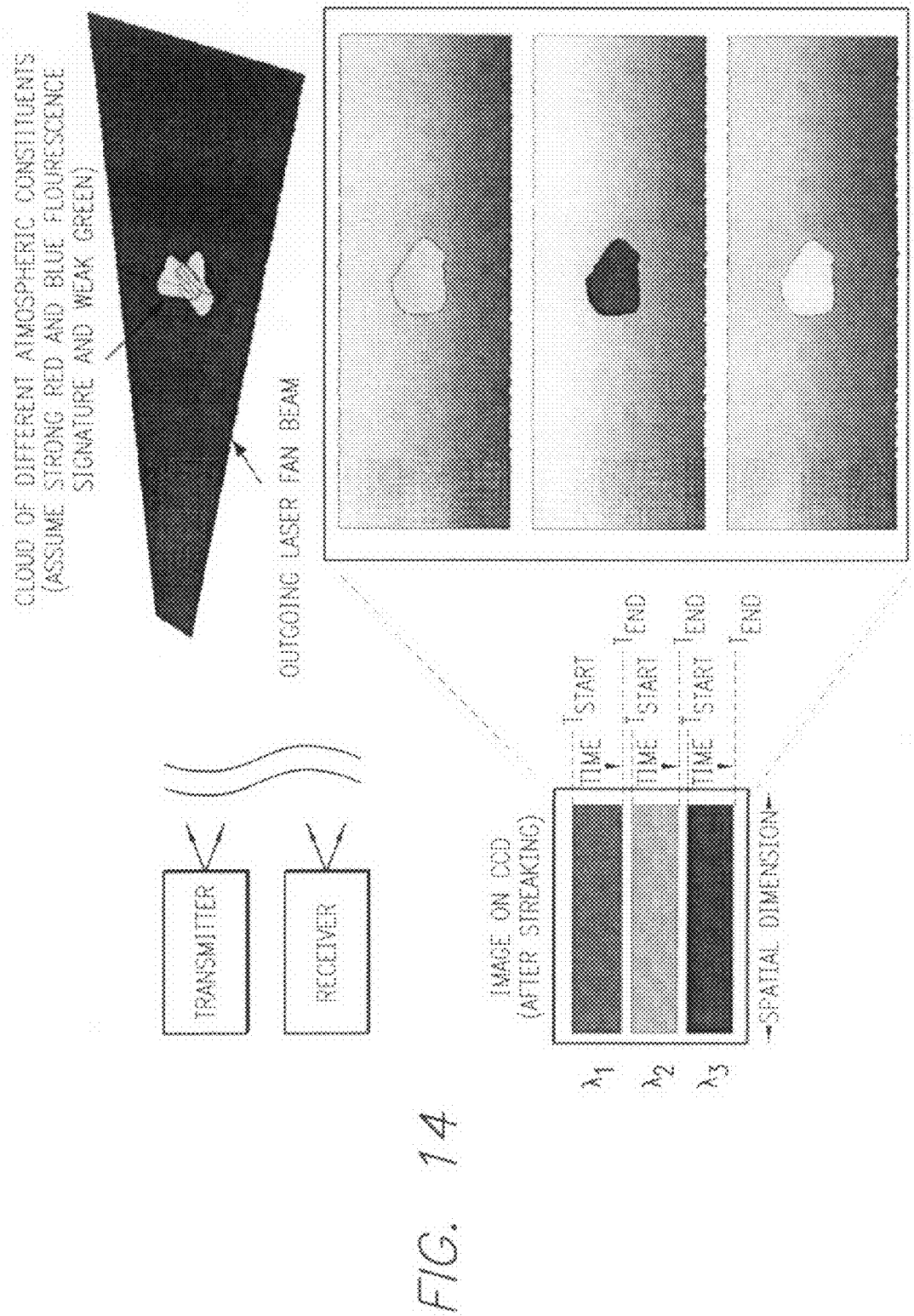
FIG. 14 is a diagram, highly schematic, of a fan beam passing through a cloud of atmospheric constituents as for analysis in the system of FIGS. 12 and 13, with the horizontal axis of the three-waveband image in the spatial dimension and the vertical axis (within each spectral band respectively) in the time dimension—in this case also range.

(a) Atmospheric constituents and contaminants—The invention passes a fan beam (FIG. 14) through a cloud of substances in the atmosphere. In the example a three-waveband system is set up, in which the fluorescence for the red and blue wavelengths is strong but the green fluorescence is weak. The horizontal axis of the three-color-band image is the spatial dimension, while the vertical axis (within each spectral band respectively) is the time dimension—which in this case also corresponds to range.

An alternative way of practicing this form of the invention is to use a plural-wavelength laser source and construct a plural-wavelength differential-imaging absorption lidar (DIAL) system. That type of system directly measures the return of the individual wavelengths, rather than looking at the fluorescence signature. (Related polarization, spectral-polarization and hyperspectral forms of the invention are discussed below in subsection 6.)

(b) Hard objects (airborne terrestrial mapping)—This type of application is related to the metropolitan-region and construction-project surveys discussed elsewhere in this document, but with important added benefits from the injection of spectral discrimination into the apparatus and procedures. A down-looking airborne system developing an image of the ground can perform several tasks simultaneously.

Figure 15:
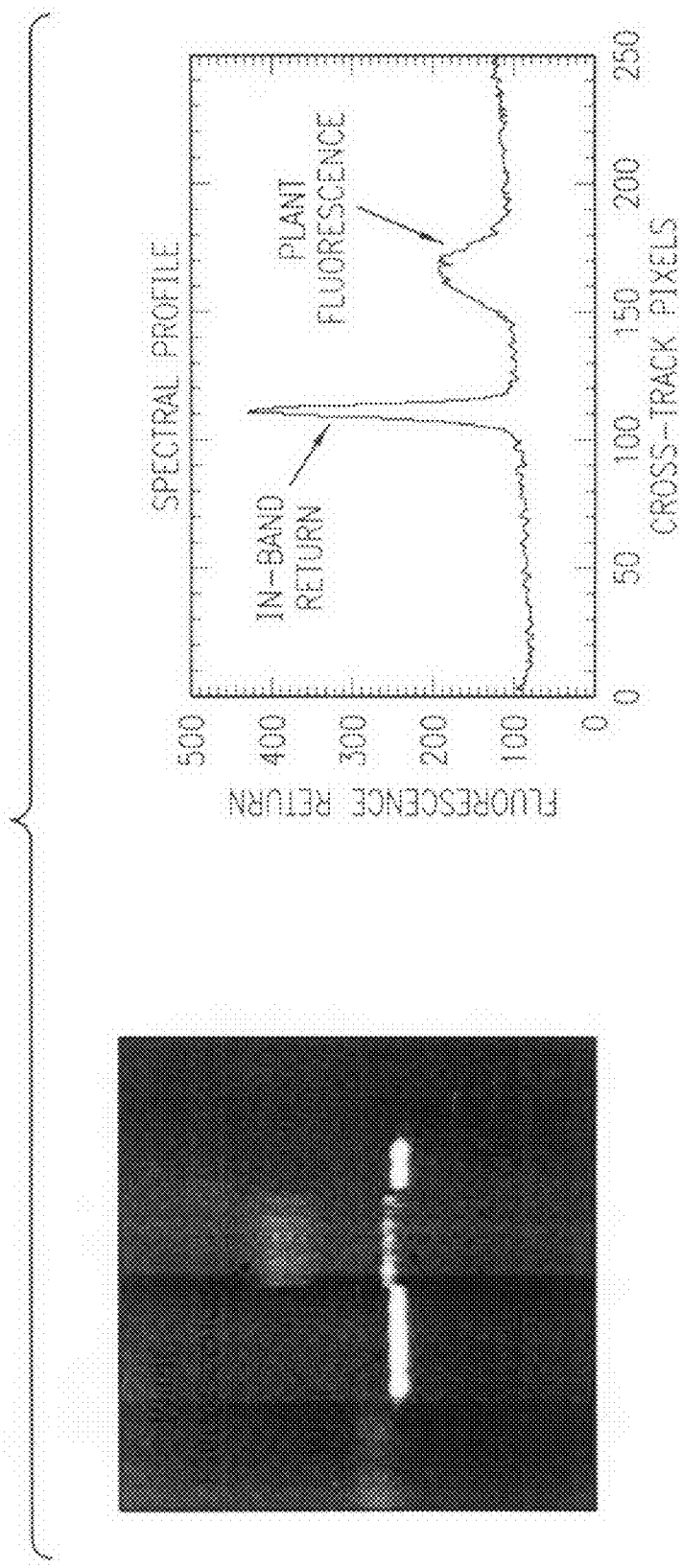
FIG. 15 is a single-frame data image, exemplary of the type of data that can be collected by the system of FIGS. 12 through 14—and at right an associated spectral profile, from which the character and quantity of the atmospheric constituents (or contaminants) can be determined.

Data that can be collected include, as an example (FIG. 15) fluorescence imaging or other DIAL-type data. The bright line in each of the wavelength regions corresponds to the ground; thus, such a system provides accurate range maps of terrain under the aircraft.

If the system is only single-wavelength, a monochromatic reflectivity map of the surface can be generated through simple consideration of the brightness of the line. In the illustration, the hump at the right of the image has a different reflectivity than the rest of the image—indicative of a different substance.

Through consideration of the different wavelengths, a spectral-spatial profile of the return can be determined. The response at different frequencies in turn can be used to determine the type of material.

In essence the system acts as an active plural- or hyperspectral system. This mode has two major benefits: (1) being active, the system is not dependent on ambient lighting and therefore can operate in day or night; and (2) the system also provides an accurate range map to the surface.

This ranging allows the user to also pick out three-dimensional shapes (i.e. including heights) of objects as well as their spectral signatures. Addition of shape information makes automatic object-recognition algorithms much easier to manage, as compared with contrast-only systems.

(c) Water-based applications—Water-based measurement environments are essentially the same as the air-based systems except that the water has a very high spectral attenuation coefficient, which changes the return signature dramatically compared with air. In addition, the water has a very high backscatter coefficient compared with air; therefore the system picks up more reflected fundamental frequencies than does an air-based system.

5. Plural-Beam Pixel Reallocations

The foregoing discussions relate primarily to resolution of a single returning beam into different wavelength bands, or rearrangement and reassembly of a single returning beam into a differently formatted image. This section instead introduces expanded capabilities that arise from transmission and recovery of more than one beam at a time.

Advanced airborne lidar concepts according to this invention are applicable to a number of methodologies for detecting and classifying marine objects that are moored, floating and resting on a shallow bottom. Such objects present a hazard to shipping and recreation, as well as having some significance to police interests and the like.

Each of the ideas presented uses the patented streak-tube imaging lidar (STIL) concept as a base, but represents a significant advancement. These forms of the present invention have important advantages over other lidar-related systems, including those familiarly known as ALMDS, Magic Lantern (Adaptation), and RAMICS.

As noted elsewhere in this document, plural-image technique can be used either for generating very high resolution three-dimensional images, or for significantly increasing the areal coverage rate of an airborne lidar system. The technique can also be used to provide area images with a single laser pulse (compared to the line images normally produced with a streak-tube system).

This capability is useful for a number of applications, including a RAMICS refinement that provides the exact depth for every pixel in the image. The conventional two-sensor design instead gives depth data for only the image center.

The preferred embodiments discussed below are not wholly independent. Rather, the embodiments are to a large extent overlapping, and many of the features taken up in one or another subsection are applicable in others as well.

(a) Fore-and-aft (or "progressive") viewing—This technique in its simplest form simply makes two or more line images on the streak tube (FIG. 18). Plural fan beams—for instance two that are pointed roughly 15 degrees forward and 15 degrees backward from the aircraft, as shown—generate the corresponding plural line images.

Fore-and-aft viewing offers a notable improvement for an ALMDS-type system. In fore-and-aft viewing the system takes two or many looks at each object, through significantly different wave structure, on a single pass and with a single sensor—thereby enabling the system to remove wave-noise errors that can seriously degrade, or completely eliminate, the signal.

Because it is extremely unlikely that the target has low SNR or highly distorted images as seen from all observing positions (FIG. 19), multiple passes over the same area are not required. Area coverage rate is therefore made very high without adding significant cost to the sensor.

While the near-surface targets (#1 and #2) suffer little change, for the surface through which imaging is assumed, it does not matter because the rays have little chance to deviate significantly. The more distorted deeper targets get significantly different looks.

Progressive viewing can also be used over dry land, for example in aid of imaging through cover—discussed elsewhere in this document—and through patchy fog and clouds.

(b) Greater operating efficiency or resolution—With a multibeam, multislit, multiimage system, many more spatial pixels can be placed in the swath of the sensor than possible with a single line. This allows a STIL-carrying aircraft to fly faster, or obtain greater resolution, or both.

Areal coverage can be increased by collecting more lines (FIG. 17[*a*]) with a single laser shot. Since aircraft speed is limited by the size of the sampled area on the surface in the direction along the track, speed can be increased—proportionally with the number of lines.

Figure 17C:
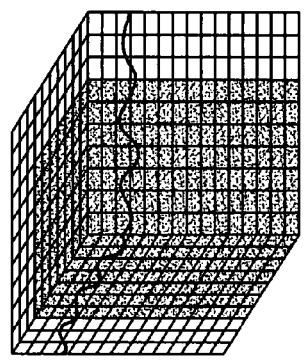
FIG. 17 is a set of three like diagrams, but representing the present invention: (a) increased areal coverage rate due to more lines per shot, (b) finer spatial resolution due to more pixels per line (shown as a magnified portion of one of the volume cubes), and (c) resolution-enhanced broader areal coverage, demonstrating both high spatial and high range resolution in a single shot.
Figure 17B:
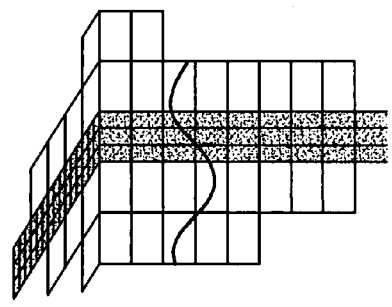
Figure 17A:
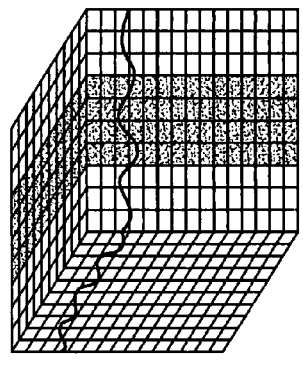

Alternatively, the additional spatial pixels can be used to provide higher-spatial-resolution images (FIG. 17[*b*]). This is accomplished by inserting the additional pixels into the same area as the original line image.

(c) Staring systems—The plural-image innovation may instead be used to provide three beams, or many, for surveying over ground. One way to exploit this advance is in stationary area imaging. Conventional streak-tube surveying requires a pushbroom system—depending on aircraft motion to sample the dimension along the track—but multiimage viewing can provide the desirable "staring" type of system mentioned earlier.

Figure 16C:
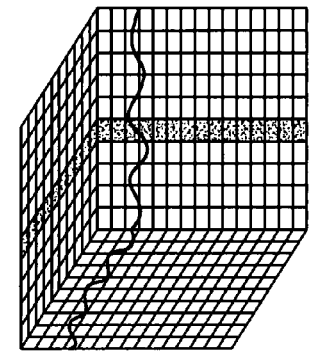
FIG. 16 is a set of three measurement-volume diagrams showing sampling regimes of different conventional lidar systems: (a) range-gated cameras with poor range resolution, that must avoid the ocean surface, (b) time-resolved detectors with poor spatial resolution, and (c) STIL systems that provide good resolution in all dimensions.
Figure 16B:
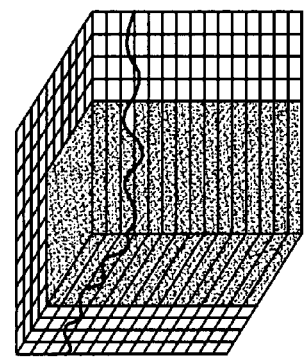
Figure 16A:
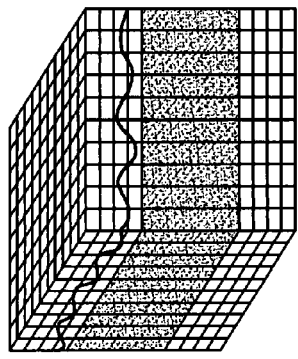

In the earlier "background" section of this document it was shown that STIL systems have powerful sampling and SNR advantages (FIG. 16) over other lidar systems. It was shown also, however, that STIL systems have been restrictively limited in the amount of data collected in each laser pulse, and hampered by the requirement for continuous translation of the instrument in a "pushbroom" mode, and also have been inadequately exploited with regard to several important commercial and industrial applications.

Thus multiimage viewing, instead of being used to provide viewing redundancy through fore-and-aft viewing as described above, can instead be used to multiply the amount of definite information acquired in each pulse. This advantage in turn can be exploited to help avoid (FIG. 17[c]) the requirement for mechanical movement of the detector, or a scanner—and also to mitigate the requirement for remapping.

(d) Lenslet arrays for remapping—For performance of area imaging and other plural-image embodiments of the invention, typically a streak-tube module need not itself be changed. Representatively the only changes are in the front-end optics, called the "remapping optics", and in the software that reassembles and interprets the CCD output.

Figure 9:
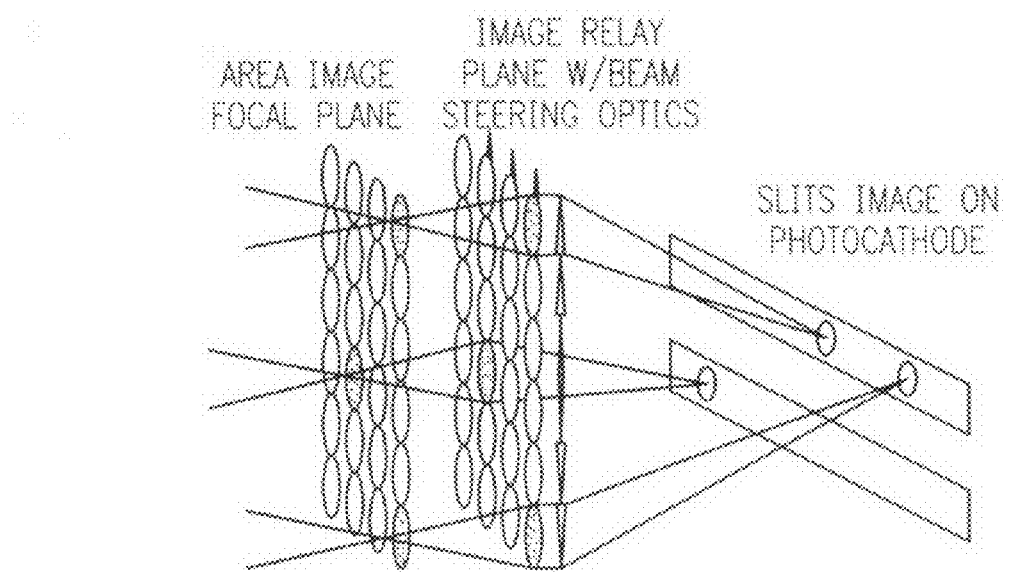
FIG. 9 is an isometric diagram, highly schematic, of lenslet-array remapping optics for a plural-slit streak-tube configuration.

As explained earlier, remapping optics convert an area image into a series of line images that can be fed into the streak tube. FIG. 9 shows a module for remapping an area image into lines using two lenslet arrays.

The first lenslet array is in the focal plane of the receiver (i.e., this is the location of the area image that is to be remapped—the size of the lenslets determines the pixel size of the receiver). These lenslets relay the pupil of the receiver onto the second set of lenslets.

It is the second set of lenslets that performs the actual remapping task, through the use of beam-steering elements. The steering elements, shown as prisms, can redirect the beam so that all of the light falls onto a selected one—or selected ones—of the slits.

The second lenslet array and its beam-steering elements are advantageously fabricated in one piece, i.e. as a single off-axis lens element. These lenslets can be made by photolithography, which is completely computer-controlled.

Both arrays are very straightforwardly manufacturable. They do have some restrictions requiring some design work, the most important being a maximum achievable ray deviation. This may dictate some compromises in a particular system design (e.g., reduced apertures of input optics, or reduced numbers of spatial pixels that can be accommodated). Very close collaboration with the optics fabricator is advisable, to define the lenslet design trade-offs in such a way as to optimize system performance.

The remapping process is otherwise completely under control of the designer. A number of system trade-offs should be strategized before settling on a final design.

The most significant of these is deciding between the density of spatial pixels and range pixels. In principle, however, several different interchangeable sets of remapping optics—each with its own associated software—can be prepared for a single streak-tube, to accommodate various data-collection environments. Once in existence, these optics/software sets can be interchanged as readily as the lenses on an ordinary SLR, video or cinema camera.

Throughput of a lenslet array may be a concern, due to fabrication details that limit the curvature of the lenses. The impact of these limitations should be examined in the detailed design of the optics.

Discussions with lenslet array vendors (such as Wavefront Sciences, Inc.) should verify in advance that reasonable throughput for the intended application is possible with existing technology and that already-occurring improvements in the state of the art are likely to eliminate any serious limitations. Also, the two lenslet arrays have to be well aligned to each other in order to work.

An alignment mechanism (either alignment fiducials or actual alignment structures, such as a post) can be built onto the array as a part of the fabrication process. Such fixtures or other provisions further distance practice of the invention from potential alignment problems.

Although as mentioned earlier a typical cost for initial lenslet design and fabrication is $20,000 per array, this amount is mostly nonrecoverable expense for setup processes. Thus subsequent copies of the lenslet array can be procured for significantly less.

Remapping for most embodiments of the present invention requires two lenslet arrays; therefore, the initial procurement is on the order of $40,000. Due to the unique requirements of this lenslet design (e.g. using two lenslet arrays in conjunction, remapping thousands of points, etc.), two separate fabrication runs should be planned to work out details and optimize system performance. Because arrays can be made of various materials, operations at longer wavelengths are feasible.

The FIG. 9 optics must provide good throughput (so that the system SNR is not degraded), and they must demonstrate the ability to survive in, e.g., the vibratory environment of a typical helicopter. Several different sets of optics should be prepared, so that the operator can resort at will to all of the methodologies discussed above—namely, high-resolution or greater area coverage, area imaging, and progressive viewing.

Each optics set should be integrated with STIL-system hardware in a modular manner for easy interchangeability as noted earlier. Lab testing should be followed by airborne ocean testing for location and characterization of realistic objects.

Once fabricated, a lenslet array is advisably mounted into an existing conventional streak-tube system in the laboratory to confirm operational area imaging. The STIL data-analysis package must be modified to accommodate the remapping matrix (i.e., the matrix of area-image pixel positions in the plural streak-tube slits) and also to account for the plural image zones on the phosphor screen (i.e., one image zone per slit as shown in FIG. 7). When these tasks are performed, single-laser-pulse three-dimensional images are generated.

Conventional STIL systems, however, are set up for wide-transverse-angle fan beams; therefore ideal practice of the invention calls for substitution of new transmitter and receiver optics better adapted for a field of view suited to three-dimensional imaging. The range-processing software that generates the three-dimensional image must be modified to work with the plural-slit configuration.

As noted earlier, remapping optics whether as lenslet arrays (FIG. 9) or as fiber-optic modules (next subsection) are not only expensive and somewhat cumbersome, but even when those drawbacks are endured are also able to collect only a very limited amount of image information. With the present invention, after an area image is remapped to a line image a three-dimensional region can be imaged—again, without requiring sensor motion or a scanner.

This is an ideal sensor for a range-gated system in which the exact range of the target can be determined, as well as the spatial position, for every pixel. This technique is also useful for a large number of applications in which true three-dimensional imaging is desired.

(e) Fiber optics for remapping—Although fiber-optic remappers as such are not at all new in STIL technology, the present invention makes fiber-optic remapping far more interesting than ever before. By virtue of the greater number of slit lengths that can be productively used with multislit imaging, as set forth in the preceding subsections, a great deal more can now be accomplished through remapping.

A large fiber redistribution network may prove difficult to build without first preparing an automated setup of some kind. A method for providing plural line images by stacking slices of large fiber tapers, however, has the potential to provide some of the desired capability without significant fixture fabrication. This has been verified in discussions with the previously noted large manufacturer INCOM.

Another approach is modular, but requires custom fixturing and may require addressing some focal-plane gaps. This approach has been confirmed in talks with Polymicro Technologies, also mentioned earlier.

In any event it is advisable to work with manufacturers to determine the best way to fabricate the devices. It is also best to have smaller, less expensive test pieces built for evaluation before ordering any final pieces.

While the earlier work of Alfano and Knight was stringently hampered as to overall number of spatial pixels, the present invention very greatly mitigates that obstacle. Given a CCD camera with 1024×1024 pixels, a user can split up the image in a number of ways, with only the constraint that the product of spatial pixels and range pixels be equal to the total number of pixels (i.e., 1024×102424, or ~1 million pixels).

As a practical matter, unused "buffer" pixels may be desired between the slit image zones; yet in most cases this consideration only slightly reduces the total number of spatial or range pixels available. Such buffer pixels ordinarily will occupy less than ten percent of the CCD.

Table 2 shows some examples of range vs. spatial pixel tradeoffs for various CCD sizes. For larger CCDs, as the table suggests, electron optics of the streak tube may dominate imaging performance.

TABLE 2

Trade-offs between the number of spatial and range pixels for given CCD size.

| CCD size | spatial-image size for indicated number of range bins | | | |
| --- | --- | --- | --- | --- |
|  | 64 bins | 128 bins | 256 bins | 512 bins |
| 1024 × 1024 | 128 × 128 | 90 × 90 | 64 × 64 | 45 × 45 |
| 2048 × 2048 | 256 × 256 | 181 × 181 | 128 × 128 | 90 × 90 |
| 4096 × 4096 | 512 × 512 | 362 × 362 | 256 × 256 | 181 × 181 |

Figure 10A:
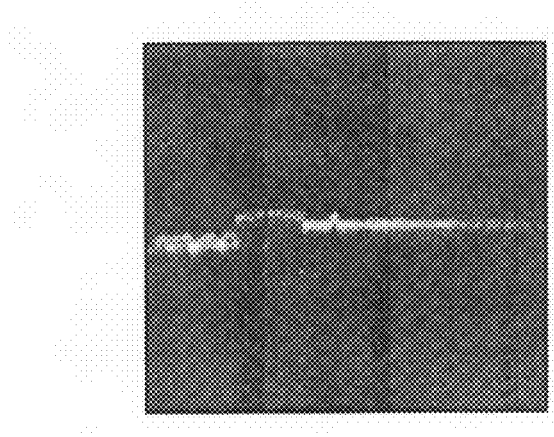
FIG. 10 is a pair of phosphor-screen images (in both sets range is vertical and a spatial dimension horizontal) for comparison: (a) conventional single-slit operation, and (b) plural-slit operation according to the invention, in particular with four slits.
Figure 10B:
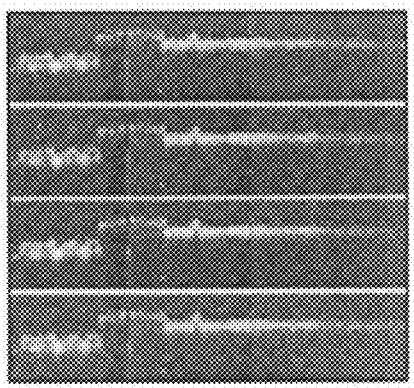

In addition to square image areas, a designer has the freedom to arrange any image area that has the same number of pixels. Given a $1024^2$ CCD and 256 desired range pixels, for example, the designer can choose a 64×64 square, a 4×1024-pixel rectangle (FIG. 10), a 4,096-pixel-by-one-line image, or virtually any other desired allocation of the available pixels.

The very great proportion of unused range pixels that is characteristic of many conventional STIL images (top and bottom in FIG. 10[a]) can be eliminated (FIG. 10[b]) through use of the invention. The PS-STIL remapping optics concept allow significant system-optimization options that are not readily available to designers using all-electronic sensors: with those devices, the designer typically cannot change the number and geometric arrangement of detector pixels.

(f) Terrestrial mapping—The potential importance of STIL application to municipal and industrial surveys has been discussed earlier. The present invention offers a key to unlocking this potential.

Cost analysis studies suggest that the invention can cover roughly five square miles per hour at a total cost of roughly $5,000 per square mile, which is considered to be very cost competitive. Thus in principle the Los Angeles area alone could generate income on the order of $10 million each year—and the effort should require only about 500 hours.

By the nature of the apparatus of the invention, this work can be done at all hours. Hence if desired the entire project, working three shifts around the clock, can be completed in only twenty days, leaving ample time for other assignments to more fully utilize a single equipment set.

Alternatively working a single shift of weekdays only, the Los Angeles mapping could be completed in sixty working days or twelve weeks—an annual duty cycle of only twenty-four percent, still allowing another three equivalent such efforts each year, and also still assuming only a single equipment set. Other metropolitan areas have similar requirements, which in the aggregate thus can provide a sustained business in airborne surveying.

The importance of using an eye-safe system bears repetition here. A significant business advantage is reduced risk and liability for eye damage, actual or claimed: physically speaking, there is essentially no possibility of such injury from an eye-safe system—though of course claims can always be made.

Another benefit is that the system can be operated at greater power. This could allow for higher-altitude flight, which would result in greater area coverage for each hour of flight.

6. Polarization and Spectral-Polarization Embodiments

A single lidar sensor that can provide several different sets of information (e.g., contrast/reflectivity images, 3-D images, and polarimetry images) is described. Because all of these different data sets are collected simultaneously, and because they are all collected from the same sensor, there are no image registration issues (i.e., difficulty in aligning data from different sensors in time or space).

Also, because this is an active system, it is not dependent on ambient lighting and can provide operation during either day or night. Finally, operation is sound at any wavelength; therefore, as previously described the system is adaptable to the eye-safe wavelength regime for deliverable systems.

Polarization forms of the invention are useful in police work for interdiction of various clandestine activities—as in fugitive pursuit and detection of drug-running or smuggling—and also for general-purpose private-sector surveying under natural but adverse viewing conditions. Such applications are discussed next. In addition to law-enforcement applications, the technology is also useful for commercial water-based applications such as bathymetry and oil-slick detection.

Figure 20A:
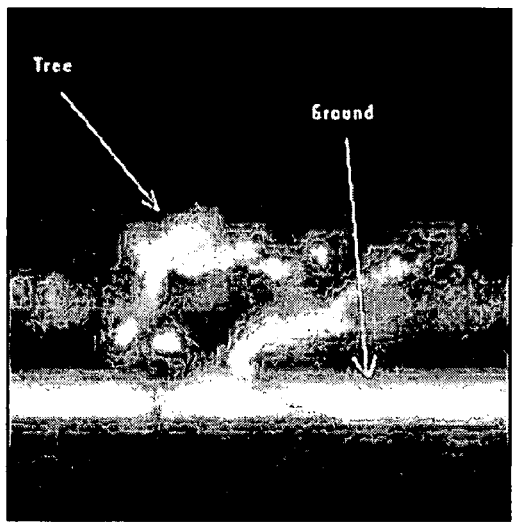
FIG. 20 is a pair of single-shot range-azimuth images through leaves: (a) light foliage on a relatively small tree, and (b) heavy foliage on a much larger tree.
Figure 20B:

(a) Imaging through diffuse cover—In the case of single-shot STIL images through trees (FIG. 20), with the system of the invention the foliage is clearly defined but the ground is also visible. Thus the 3-D STIL polarimeter can detect objects under such cover.

One of the benefits of a monostatic lidar system is that the system transmits and receives through the same opening in a screening/covering medium. Therefore it can register an object under a forest canopy, whereas a simple imaging system fails—at least intermittently—in such a situation because the image is fragmented by the screening media.

(b) Covered hard objects—Range and polarimetry data can provide a clear distinction between an object and the ground, the first by height and the second by polarization effects. While complete reconstruction of the object may be impeded by blocking effects of the cover, general size and overall polarization signature can still be estimated.

Any artificial covering such as a tarpaulin or netting potentially has polarization signatures significantly different from those of the background, due to the significantly different materials. A 3-D imaging polarimeter has the potential to provide an excellent countermeasure to most forms of covering—and especially netting in that it can both detect that covering and separate its signature from that of an object beneath.

As an example, consider detection of a domed hard object, well-covered but intersected (FIG. 21[a]) by a STIL fan beam. The object is assumed to be only slightly different in reflectivity, but has a significant polarization effect on the return light.

Here the horizontal axis of the dual-slit polarimetry image is the spatial dimension (FIG. 21[b]) while the vertical axis—within each polarization state analyzer (PSA) band—is the time dimension, which also corresponds to range. Three maps (FIG. 21[c]) are produced by the sensor, illustrating how difficult it would be for a criminal to effectively hide the object from this system.

Although the cover is very effective in concealing the object in a simple reflectivity image (similar to what would appear in an ordinary photo), the different polarization returns clearly reveal an object of differing material—and the conspicuous hump caused by the object in the range direction adds emphasis to the polarization data.

Reconstructed images from multiple shots illustrate the advantage of acquiring both polarization and range data in addition to reflectivity. The PS-STIL 3-D polarimeter, described in the next section, captures all these data in a single laser pulse.

Analysis of the data is performed using Mueller matrix techniques documented earlier. These analyses are performed as described in the technical literature—but they all come down to creating at least two independent measurements (i.e., two equations in two unknowns).

Figure 22:
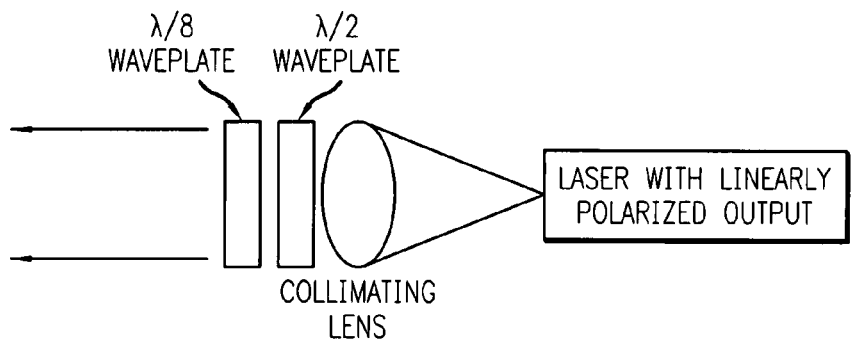
FIG. 22 is a diagram, highly schematic, of transmitter optics for a preferred embodiment of a polarization form of the invention—wherein the half-wave ("$\lambda/2$") plate allows the linear polarization to be rotated arbitrarily and the eighth-wave ("$\lambda/8$") plate creates the desired elliptical polarization state.
Figure 23:
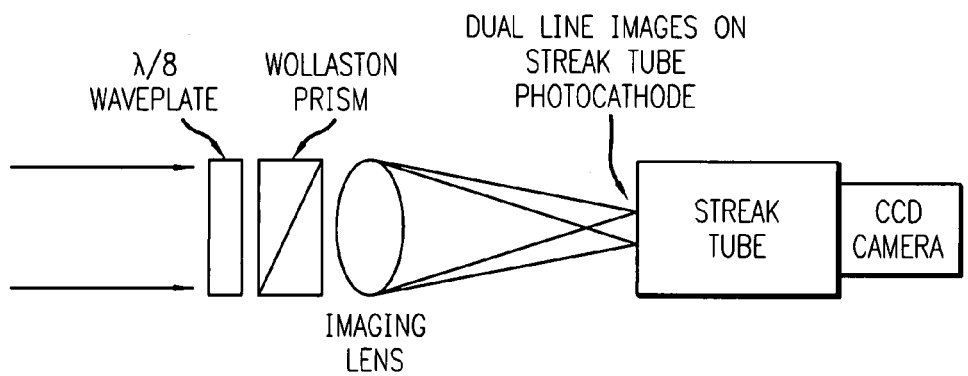
FIG. 23 is a like diagram of complementary receiver optics for the same embodiment—the $\lambda/8$ plate and Wollaston prism being polarization-state analyzers that produce the two measurements necessary to determine the degree of polarization of the return beam.

(c) PS-STIL polarimeter design—As can be seen from a preferred implementation of the instrument for the example given above (FIGS. 22 and 23), the simplicity of the device (i.e., few optics and no moving parts) is one of the most appealing aspects of the PS-STIL approach. As the receiver polarization-state analyzer splits the incoming beam into two separate polarization states, the polarization-state generator in the transmitter has to produce only one state.

Because the two polarization states in the receiver are typically produced by a polarizer at two orthogonal settings (e.g., the two polarizer settings, −72.385° and −162.385°, are 90° apart), the rotating polarizer can be replaced with a fixed Wollaston prism. This prism, which is a commonly available polarization component, splits the two polarization states by adding an angular displacement to one polarization as compared to the other.

The angular displacement is translated into a spatial displacement by the imaging lens, which forms two separate images on the streak-tube photocathode that go into two separate slits. Other polarization elements (e.g., beam-splitters, Brewster windows, etc.) can achieve a similar polarization split, but the Wollaston is preferred for this example.

This instrument uses a fan-beam illumination pattern. It produces three maps of the area under investigation: (1) a contrast (or reflectivity) map at the wavelength of the sensor; (2) a degree of polarization (DP) map that shows how the target and surroundings affected the polarization of the transmitted light;

TABLE 3

Features and benefits of the 3-D imaging polarimetry system.

| Feature | Benefit |
| --- | --- |
| sensor provides data from three different physical mechanisms for interacting with targets and clutter | Significantly improves detection and clutter reduction. Segmentation, the method for determining which pixels are object and which are background, is significantly enhanced by looking for correlation in all three images. Algorithm development, analysis, and visualization are simpler than for hyperspectral systems |
| range data | Provides 3-D shape of target. Allows separation of screening/camouflage from target. Allows imaging through forest canopy. |
| contrast data | Provides standard imagery, easy to evaluate and process. |
| polarimetry data | Difficult to provide camouflage as paint typically has distinct polarization characteristics. |
| one receiver and one transmitter | Sensor is compact. Sensor is less complex. Sensor is more reliable. |
| no moving parts | Sensor is more reliable. |
| simultaneous collection of all three data sets in one receiver | Spatial and temporal registration of the data sets is not an issue. | and (3) a range map that has the 3-D shape of a detected object and its surroundings.

These three maps interact with the object and the surroundings in fundamentally different ways; therefore the clutter signatures are different (and often uncorrelated). In addition, it is difficult to conceal an object from all three of these detection methods at once; consequently countermeasures are difficult. Table 3 summarizes benefits of the three-dimensional-imaging polarimetry system.

(d) Spectral polarimetry—A plural-spectral version of the instrument is discussed above. Here a hyperspectral version is presented, combined with a polarimeter to provide single-laser-pulse spectral-polarimetry data.

The sort of data collected from the hyperspectral form of the instrument appears in FIG. 24. The receiver is identical in construction to the plural-spectral form except that the dispersive element is rotated 90 degrees, so that wavelengths are spread alone rather than perpendicular to the slit.

In this case the transmitter emits a pencil beam, rather than a fan beam. A plural-slit hyperspectral version of the instrument can be implemented by transmitting plural pencil beams at the same or different wavelengths (one per slit).

The spectral-polarimetry (SP) form of the instrument is a combination of the hyperspectral and polarization forms described above. The laser transmitter is identical to that used for polarimetry, and the receiver has both the polarization optics and the wavelength dispersion optics in front of the lens.

This form of the instrument has the potential to allow truly unique data capture for a variety of applications. For atmospheric constituents the combination of fluorescence spectral strength combined with polarization data provides potentially great discrimination capability against a variety of chemical and biological species.

Biological materials are known to have variations in fluorescence lifetime ranging from 100 psec and 10 nsec. Temporal resolution of the elastic backscatter and the fluorescence from nanosecond laser pulses provides the capability of discriminating objects by measuring their fluorescence lifetimes.

In the hyperspectral mode, operator-controlled timing parameters for the streak tube determine the resolution of the range information and the distance in space over which the range information is collected. When the streak tube sweep extends less than a meter in front of and beyond the target, the streak tube time-resolves the return laser pulse and the fluorescence return.

In such circumstances, the lifetime of the induced fluorescence can be measured. Fluorescence lifetime measurements are an additional discriminant that may be beneficial for identification of biological agents.

Figure 28C:
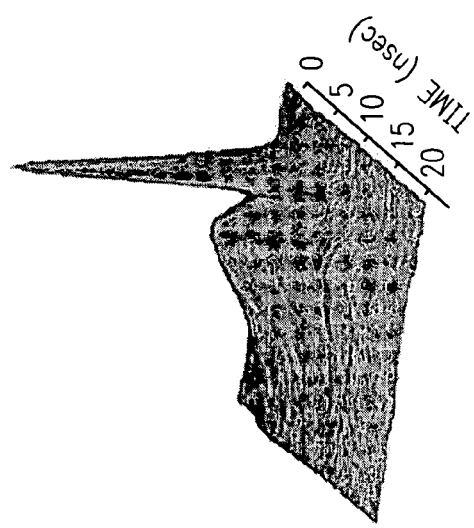
FIG. 28 is a set of three images relating to time-resolved laser pulse and fluorescence return (a) from a highly fluorescent plastic cable tie, with the two 3-D views of the data in (b) and (c) showing the elastic return from the laser pulse, followed by the longer fluorescence return: the gray lines locate the wavelength of maximum return as a function of time (vertical plot) and the time of maximum return as a function of wavelength (horizontal plot)
Figure 28B:
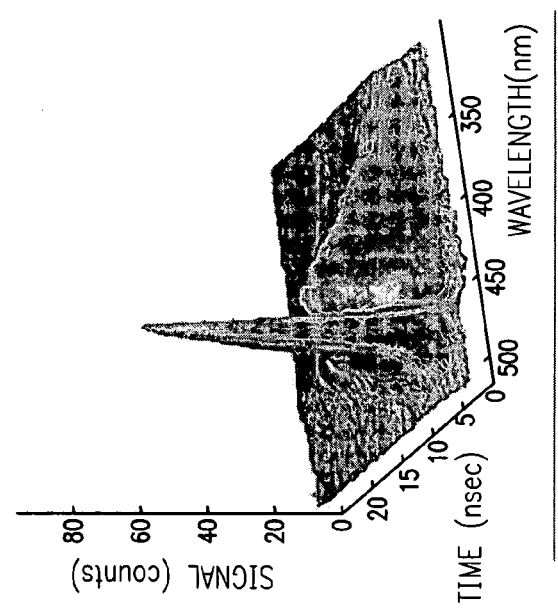
Figure 28A:
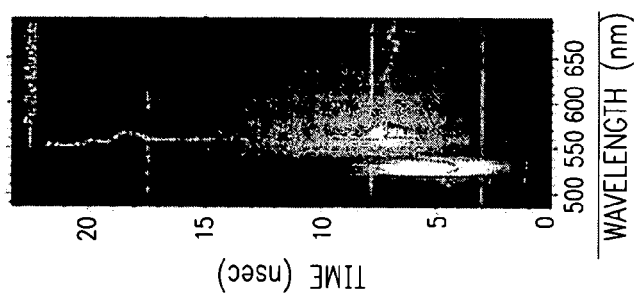
Figure 29A:
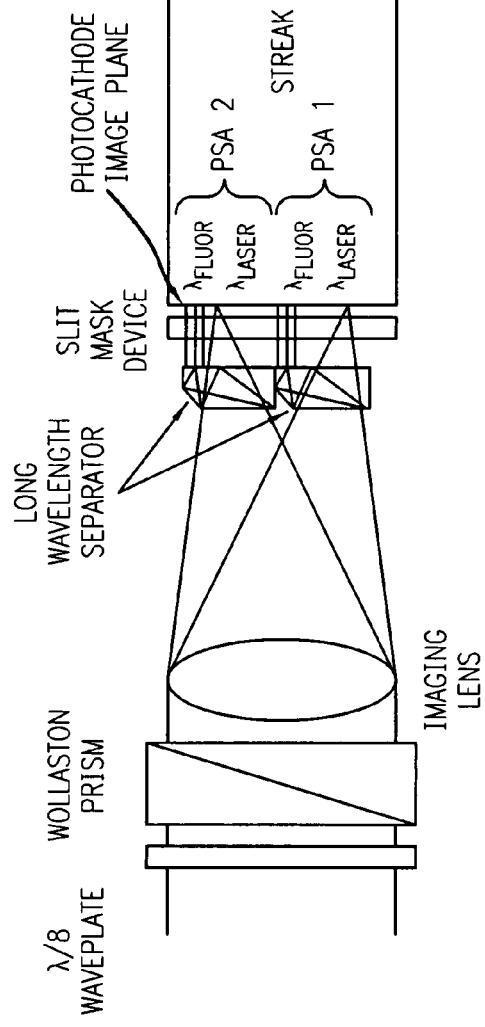
FIG. 29 is a set of three illustrations relating to a combined STIL polarimeter and fluorescence sensor: (a) is a diagram comparable with FIG. 12 etc. showing the front-end optics for an electron-tube system, (b) an enlarged detail view of beam-splitter optics at a fiber-optic faceplate that transfers the long-wavelength image to the actual image plane, and (c) a diagram of the combined sensor data as imaged on the photocathode slits.
Figure 29C:
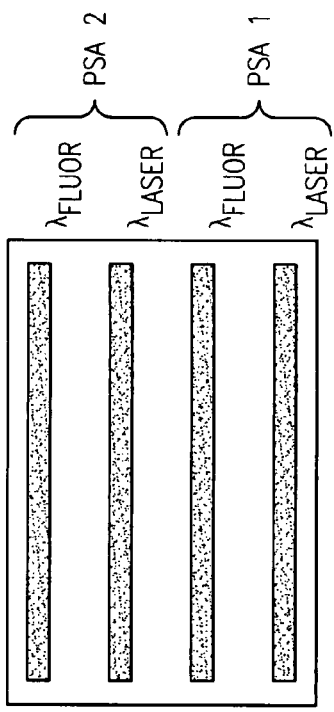
Figure 29B:
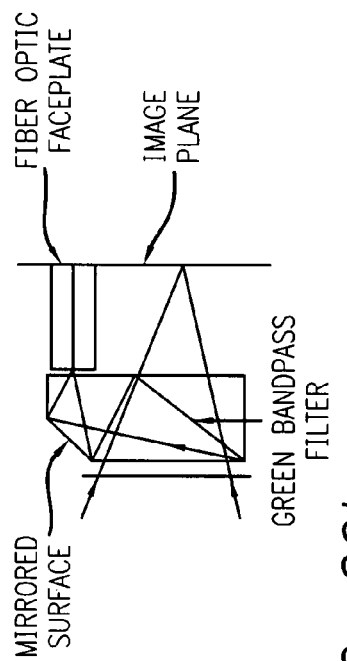

With such a measurement arrangement, different views of data (FIG. 28) collected from a single laser pulse contain the elastic backscatter and induced fluorescence return as a function of wavelength and time. In the illustrated example, the tall, narrow peak is the time-resolved elastic backscatter from the 9 ns excitation pulse at 532 nm.

The broadly sloping region is the time-resolved induced fluorescence. The induced fluorescence is delayed in time with respect to the excitation pulse and lasts more than twice as long as the excitation pulse.

Yet another extremely powerful hybrid instrument (FIG. 16) enables simultaneous acquisition of polarimetric data together with fluorescence information. Here polarization data are collected in two slits, and all other wavelengths through another pair of slits.

Such a system detects whether fluorescence occurred, but provides no further spectral-discrimination capability. Other configurations can provide significantly more spectral data.

For example, the fan-beam transmitter can be replaced with a pencil beam, and the spectrum analyzed as for the hyperspectral configuration—analogously to the fluorescence-lifetimes system discussed just above. Multiple slits can then be used for different-wavelength transmitter beams, or for multiple polarization states.

7. A Gigahertz Wavefront Sensor

This system, although based upon an array of subapertures and resulting indicator-beam spot positions analogous to those used in the conventional Hartmann-Shack sensor discussed earlier, is a major advancement over that Hartmann-Shack system. In order to take advantage of the speed of the streak tube, the light from each sub-aperture has to be split up in a way that it is possible to both measure the spot position and also direct the light onto at least one slit—thereby enabling streaking, so that the indicator-beam positions can be time resolved.

Figure 27:
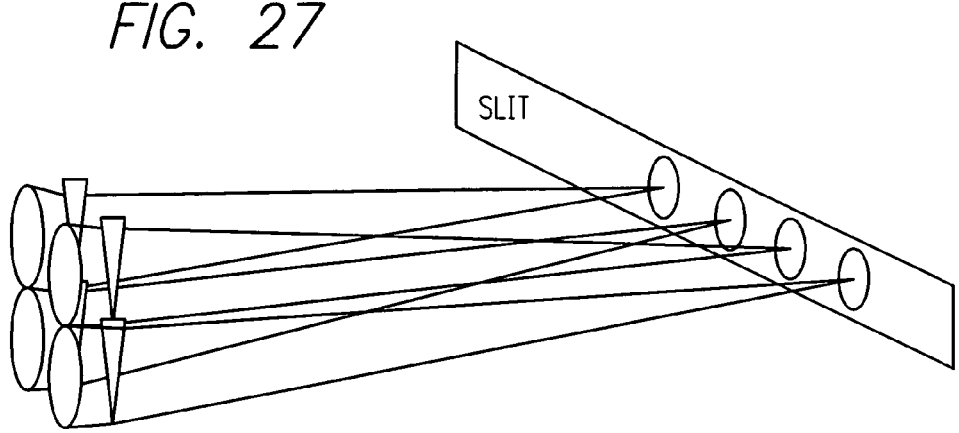
FIG. 27 is an optical quad cell, according to the present invention, that performs the function of the conventional cell of FIG. 16 and also redirects the indicator subbeams onto a slit for the streak tube.
Figure 25:
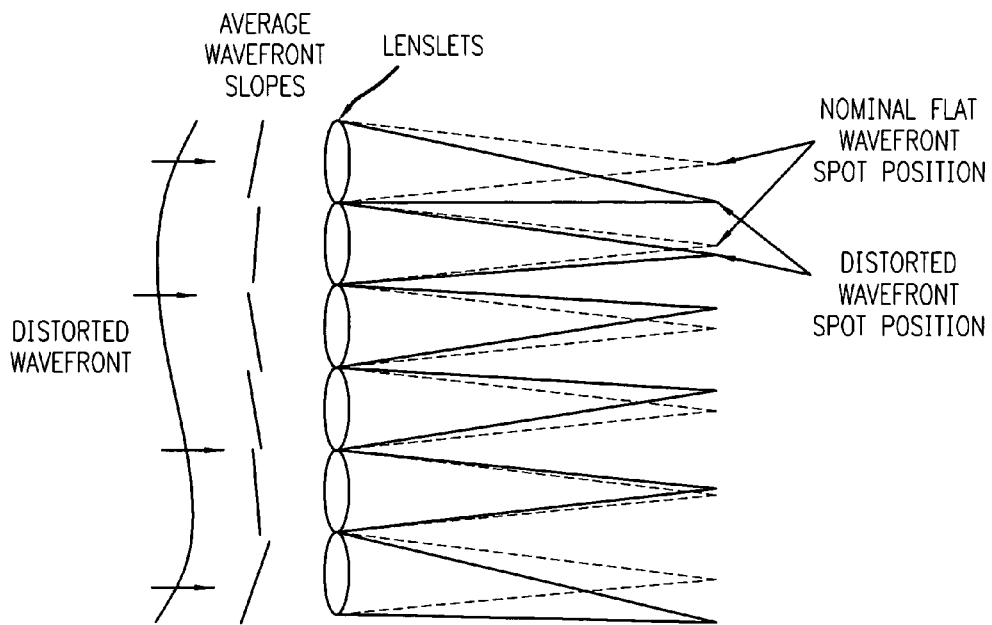
FIG. 25 is an elevational diagram, highly schematic, of a conventional Hartmann-Shack wavefront sensor (WFS) that directs subbeams to a conventional quad cell to indicate wavefront angle.
Figure 26:
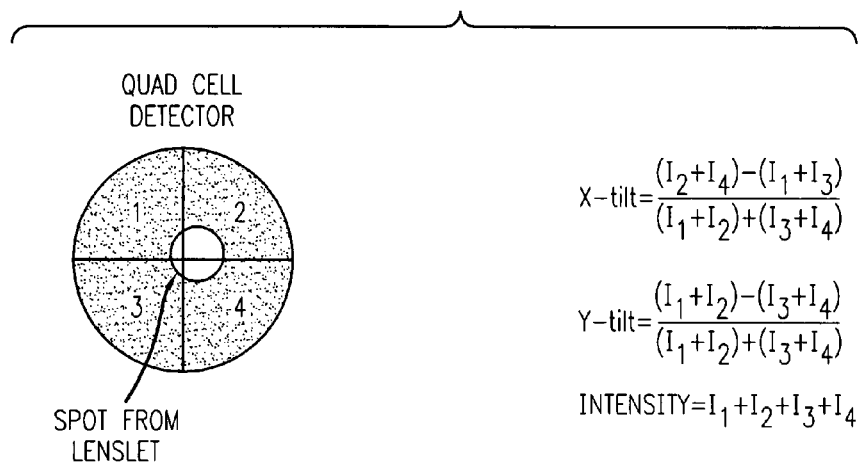
FIG. 26 is a conventional quad cell as used in a Hartmann-Shack WFS to measure spot position (which corresponds to the three-dimensional tilt of the wavefront) and intensity.

(a) Principles of the system—Precisely this capability is achieved by adding a second set of lenslets (FIG. 27) that serves as an array of optical quad cells. Each of these cells collects the light from a corresponding respective group of four lenslets in the first array—and then redistributes the light onto a slit.

This redistribution is invoked by proper selection of the lenslet focal length and—in effect—the strength of an associated prism that is used to "steer" the light onto the slit. In practice, however, there is no separate prism as such; rather, the lenslet and prism are an integrated single-element optic (i.e. an off-axis lens element).

The light reaching the slit is then streaked, to provide time resolution of the linear array of indicator beams mentioned above—and thus of the three-dimensional tilts of all the subapertures whose indicators are directed to the slit. It is this stage, in particular, which achieves the previously noted improvement in time resolution by five orders of magnitude. This system, using a single slit, is believed to be novel and is within the scope of certain of the appended claims.

(b) Plural-slit enhancement—A single-slit embodiment, however, is not the end of the matter—for the number of individual wavefront elements that can be sensed and time resolved in this way is somewhat limited. To obtain a truly excellent result, the preferred system also incorporates the plural-slit feature described above and thereby at least doubles the spatial resolution across the wavefront to be sensed.

Ideally multiple slits are used, and a corresponding multiple thereby imposed upon the number of wavefront regions whose orientations can be independently measured. As a result this gigahertz wavefront sensor (GHz WFS) is able to measure both the intensity and the phase of laser light with extraordinarily high resolution in both time and space.

Furthermore this instrument collects all the information in a single laser pulse (i.e., it does not require multiple pulses to assemble information). In this way the system eliminates any pulse-to-pulse variations that would compromise the data.

With this instrument, designers, modelers, and users of high-power short-pulse lasers now have access to data that can be directly compared to information from their design models and simulations. This allows much greater confidence in the design, and allows the models and designs to be experimentally validated.

In particular, transient "hot spot" events (intensity peaks in single pulses which reach the damage threshold of the optics)—and which are often blamed for the degradation of laser performance—can now be fully captured. Conventional laser instrumentation would be able to do no more than determine that such an event has occurred. For instance, an oscilloscope trace might show a narrow bright peak, or a laser-characterization instrument might show a hot spot in the intensity image—but they fail to provide phase and intensity information at high spatial and temporal resolution, as the present invention does, and therefore cannot enable a full causal assessment.

Laser manufacturers can use these several types of new information to provide far better control over their design and fabrication processes—and consequently can greatly improve laser reliability and performance—by virtue of the enormously superior diagnostic capabilities that this sensor provides. All applications using high-power short-pulse lasers will in turn benefit from better lasers resulting from use of the GHz WFS.

(c) Pixel allocation—The number of subapertures that can be sampled (and thus the spatial resolution) is limited by several parameters: the dimensions of the CCD camera on the back of the streak tube, the pulse length, and the desired time resolution of the samples. If the GHz WFS were implemented with conventional streak-tube imaging, as noted above the user could only get the number of pixels that would fit across one slit.

Plural-slit streak-tube imaging allows a great deal more flexibility in the manner in which pixels are allocated in space and time. An example of the way in which pixels can be assigned to slits will now be presented—and is very interesting in that it serves as an example for many plural-slit systems other than the WFS. In particular, the discussion below also represents a methodology for determining system limits and organizing the process of pixel-to-slit allocation for essentially all the PS-STIL embodiments introduced in this document.

Consider a camera with 1024×1024 pixels on the back of the streak tube, together with a laser having a 5 ns FWHM average pulse length. The spatial and temporal resolution limits of the system are now clear—they are given by:

$$4P_S P_T \leq P_{CCD},$$

where $P_S$ is the number of spatial subapertures (the factor of 4 is due to the fact that each spatial subaperture requires the four quad cell measurements), $P_T$ is the number of samples in time per pulse, and $P_{CCD}$ is the total number of pixels in the CCD (i.e., roughly 1,000,000).

$P_t$ is the total sample length divided by the sample period. Most of the energy is ordinarily in a time corresponding to 6 FWHM (full width at half maximum) of the pulse; therefore, the equation becomes $$4P_S \cdot 6FWHM / T_S \leq P_{CCD},$$

where $T_S$ is the amount of time per sample. Putting in the numbers gives $$P_S \leq 8333 T_S,$$

where $T_s$ is in nanoseconds. Thus, if 1 nanosecond samples are desired, the GHz WFS can have 8333 subapertures (i.e., approximately a 90×90 spatial sampling of the laser beam). where $T_S$ is in nanoseconds. Thus, if 1 nanosecond samples are desired, the GHz WFS can have 8333 subapertures (i.e., approximately a 90×90 spatial sampling of the laser beam).

Since there are 1024 pixels in the camera, the optics can be set up to provide 8 slits that are 1024 pixels wide. A conventional streak-tube imaging system, which can only use one slit, would only provide 1024 spatial samples—forcing all of the other pixels to be in the time dimension. Plural slits thus provide much more flexibility and capability.

This description is based upon theoretical maximum resolution. In actual usage, the numerical result may be reduced by ten to twenty percent, to provide some visual buffer zones between pixels.

Performance of all forms of the present invention is unusually and extremely sensitive to any individual component deficiencies. For this reason all components should be carefully tested individually to determine whether they meet their respective specifications before attempting to assemble and operate the system.

Also highly advisable is initial system testing in a laboratory setting. Radiometry, resolution, and noise tests and analyses should establish whether the system meets specifications before essaying field operation. Field testing, when it is appropriate, should be performed both in aircraft and in a ground-based vehicle.

For an effective assessment it is advisable to independently model the expected system performance (radiometry, resolution, and noise). Comparison of a model with measurements taken in the lab and in the field, as prescribed above, is very informative. Modifications to the model, and validation against the data, may then be necessary. It is also essential to modify any existing STIL data-analysis software straightforwardly to work with the PS-STIL of GHz WFS data.

It will be understood that the foregoing disclosure is intended to be merely exemplary, and not to limit the scope of the invention—which is to be determined by reference to the appended claims.

I claim:

1. A spatial mapping system for mapping a region; said system comprising:
    a light source for emitting at least one thin, fan-shaped beam from a moving emission location toward such region, a thin dimension of the beam being oriented generally parallel to a direction of motion of the emission location;
    an imaging device for receiving light reflected from such region and forming an image of the reflected light;
    means for separating the reflected light to form plural reflected beam images representing different aspects of such region, respectively; and
    an image-responsive element for receiving and responding to the plural beam images.

2. The system of claim 1, wherein:
    the separating means comprise means for discriminating between spatially different aspects of such region.

3. The system of claim 1, wherein:
    the separating means comprise means for discriminating between aspects of such region that are carried in portions of the beam received at different angles.

4. The system of claim 3, wherein:
    the discriminating means comprise means for forming discrete plural reflected beam images from portions of the beam received at different angular ranges, respectively.

5. The system of claim 1, wherein:
    the separating means comprise means for discriminating between aspects of such region that are carried in different polarization states of the beam.

6. The system of claim 1, wherein:
    the separating means comprise means for discriminating between aspects of such region that are carried in different spectral components of the beam.

7. The system of claim 1, wherein:
    the separating means comprise means for discriminating between combinations of two or more different aspects of such region that are carried in different characteristics of the beam, at least one of which characteristics is selected from among:
    spatially different aspects of the beam,
    different polarization states of the beam, and
    different spectral components of the beam.

8. The system of claim 7, wherein:
    at least two of said characteristics are selected from said spatial, polarization and spectral characteristics.

9. The system of claim 1, wherein the emission location is selected from the group consisting of:
    a spacecraft;
    an aircraft;
    another type of vehicle; and
    another type of moving platform.

10. The system of claim 1, wherein:
    the emission location is a fixed light source cooperating with a scanning system to provide a moving image of the light source.

11. The system of claim 1, wherein:
    the light source comprises means for emitting the at least one beam into such medium that is a generally clear fluid above a generally hard surface.

12. The system of claim 1, wherein:
    the light source comprises means for emitting the at least one beam into such medium that is a turbid medium, including but not limited to ocean water, wastewater, fog, clouds, smoke or other particulate suspensions.

13. The system of claim 1, wherein:

the light source comprises means for emitting the at least one beam into such medium that is a diffuse medium, including but not limited to foliage at least partially obscuring a landscape.

14. A spatial mapping system for mapping a region; said system comprising:

a light source for emitting a beam whose cross-section has an aspect ratio on the order of 1:1, from a moving emission location toward such region;

an imaging device for receiving light reflected from such region and forming an image of the reflected light;

means for separating the reflected light to form plural reflected beam images representing different aspects of such region, respectively; and an image-responsive element for receiving and responding to the plural beam images.

15. The system of claim 14, wherein:

the imaging device comprises means for receiving the reflected light from such region as a reflected-beam whose cross-section has an aspect ratio on the order of 1:1.

16. A spectrometric analytical system for analyzing a medium with any objects therein; said system comprising:

a light source for emitting substantially at least one pencil beam toward such medium;

an imaging device for receiving light reflected from such medium and forming an image of the reflected light;

means for separating the reflected light along one dimension to form plural reflected beam images arrayed along said dimension and representing different aspects of the medium, respectively;

optical-dispersing means for forming a spectrum from at least one of the plural images, by dispersion of the at least one image along a dimension generally orthogonal to the said dimension; and an image-responsive element for receiving and responding to the plural beam images.

17. The system of claim 16, wherein:

the dispersing means comprise means for forming a spectrum from each of the plural images, respectively.

18. The system of claim 16, wherein:

the separating means comprise means for separating the reflected light to form plural images representing spatially different aspects of the beam, respectively.

19. The system of claim 16, wherein:

the separating means comprise means for separating the reflected light to form plural images representing different polarization states of the beam, respectively.

20. The system of claim 16, wherein:

the separating means comprise means for separating the reflected light to form plural images representing different spectral constituents of the be am, respectively.

21. The system of claim 16, wherein:

the separating means comprise means for separating the reflected light to form plural images representing combinations of two or more different aspects of such medium that are carried in different characteristics of the beam, at least one of which characteristics is selected from among:

spatially different aspects of the beam, different polarization states of the beam, and different spectral components of the beam.

* * * * *